US010376550B2

(12) United States Patent
Bright

(10) Patent No.: US 10,376,550 B2
(45) Date of Patent: Aug. 13, 2019

(54) NUTRACEUTICAL COMPOSITION AND METHODS OF USE

(71) Applicant: Dacy Tech Party Ltd., Delacombe (AU)

(72) Inventor: Dan Bright, Delacombe (AU)

(73) Assignee: Dacy Tech Pty Ltd., Delacombe (AU)

(*) Notice: Subject to any disclaimer, the term of this patent is extended or adjusted under 35 U.S.C. 154(b) by 458 days.

(21) Appl. No.: 15/090,556

(22) Filed: Apr. 4, 2016

(65) Prior Publication Data

US 2016/0228481 A1    Aug. 11, 2016

Related U.S. Application Data

(63) Continuation-in-part of application No. 12/812,488, filed as application No. PCT/AU2008/001834 on Dec. 12, 2008, now abandoned.

(30) Foreign Application Priority Data

Dec. 12, 2007    (AU) ................ 2007906771

(51) Int. Cl.
   *A61K 36/14*    (2006.01)
   *A61K 35/60*    (2006.01)
   *A61K 35/618*    (2015.01)

(52) U.S. Cl.
   CPC .............. *A61K 36/14* (2013.01); *A61K 35/60* (2013.01); *A61K 35/618* (2013.01)

(58) Field of Classification Search
   None
   See application file for complete search history.

(56) References Cited

U.S. PATENT DOCUMENTS

| | | | |
|---|---|---|---|
| 4,473,551 A | 9/1984 | Schinitsky | |
| 6,576,271 B2 | 6/2003 | Nair et al. | |
| 2003/0044470 A1 | 3/2003 | Wani et al. | |
| 2004/0228850 A1 | 11/2004 | McEwen | |
| 2004/0248821 A1 | 12/2004 | Ziegler | |
| 2006/0105055 A1* | 5/2006 | Marenick | A61K 8/345 424/581 |
| 2011/0045099 A1 | 2/2011 | Bright | |

FOREIGN PATENT DOCUMENTS

| | | | |
|---|---|---|---|
| CN | 1304988 A * | 7/2001 | |
| CN | 1611237 A | 5/2005 | |
| KR | 20060016163 | 2/2006 | |
| WO | 9605164 A1 | 2/1996 | |
| WO | WO-03089399 A1 * | 10/2003 | .......... C07C 51/48 |

OTHER PUBLICATIONS

Calder et al. Curr Opin Clin Nutr Metab Care. Mar. 2001;4(2):115-21 (abstract only). Retrieved from <URL: https://www.ncbi.nlm.nih.gov/pubmed/11224655> on Oct. 12, 2018. (Year: 2001).*
Pearson, et al., "Effects of simulated digests of *Biota orientalis* and a dietary neutraceutical on interleukin-1-induced inflammatory responses in cartilage explants", American Journal of Veterinary Research, 2008, vol. 69, pp. 1560-1568., 9 pages.
Choi, et al., "A pinusolide derivate, 15-methoxypinusolidic acid from *Biota orientalis* inhibits inducible nitric oxide synthase in microglial cells", International Immunopharmacology, 2008, vol. 8, pp. 548-555, 8 pages.
Zhu, et al, "Effects of *Biota orientalis* extracts and its flavonoid constituents, quercetin and rutin on serum uric acid levels in oxonate-induced mice and xanthine dehydrogenase and xanthine oxidase activities in mouse liver." Journal of Ethnopharmacology, 2004, vol. 93, pp. 133-140, 8 pages.
Pearson, et al, "Anti-inflammatory and Chondroprotective Effects of Nutraceuticals from Sasha's Blend in a Cartilage Explant Model of Inflammation", Molecular Nutritional Food Research, Mar. 2007, vol. 51, pp. 1020-1030, 11 pages.
Lai, et al., "Dietary *Platyclaudus orientalis* Seed Oil Supresses Anti-Erythrocyte Autoantibodies and Prolongs Survival of NZB Mice", Clinical Immunology and Immunopathology, 1994, vol. 71, pp. 293-302, 10 pages.
Yoshida, et al., "Dietary *Juniperis virginiensis* Seed Oil Decrease Pentobarbital-associated mortalities among DBA/1 Mice Treated with Collagen-adjuvant Emulsions", Journal of Lipid Mediators Cell Signalling, 1996, vol. 13, pp. 283-2935, 12 pages.
Jie, et al., "Lipids in Chinese Medicine Characterization of all cis 5,11,14,17-eicosatetraenoic Acid in *Biota orientalis* Seed Oil and a study of Oxo/Furanoid Esters Derived from *Biota Oil*", Journal of American Oil Chemists Society, Apr. 1988, vol. 65 (4), pp. 597-600, 4 Pages.
Mr. Kent's Chemistry Page, "Like Dissolves Like and Molecule Ion Attractions", www.kentchemistry.com/links/bonding/likedissolveslike.htm, Retrieved from the Internet on May 8, 2015, 2 pages.
International Search Report and Written Opinion for PCT Application No. PCT/AU2008/001834, dated Feb. 25, 2009, 20 pages.
Cohen, et al. J Rheumatol, "A randomized, double blind, placebo controlled trial of a topical treatment containing glucosamine sulfate, chondroitin sulfate, and campher for osteoarthritis of the knee", Mar. 2003; 30(3) 523-528, Abstract.
"Osteoarthritis" definition, http://www.mayoclinic.org/diseases-conditions/osteoarthritis/basics/definition/con-20014749, Internet Archive Date Oct. 13, 2011, Retrieved on Apr. 4, 2016, 3 pages.
"Economic Importance of Thuja orientalis", www.greencleanguide.com/2012/06/2010, Internet Date Jun. 10, 2012, 1 page.

* cited by examiner

*Primary Examiner* — Amy L Clark
(74) *Attorney, Agent, or Firm* — ARC IP LAW, PC; Joseph J. Mayo

(57) ABSTRACT

A method of modulating inflammation in an organism, which includes administering to an organism a composition including a therapeutic amount of a hydrolyzed extract from the plant *Biota orientalis*. Several key components of the hydrolyzed extract of *Biota orientalis* have been identified that have also been shown to have an effect in dramatically reducing inflammatory responses.

9 Claims, 19 Drawing Sheets

Specification includes a Sequence Listing.

| Porcine Gene | Accession No. | Forward primer | Reverse primer |
|---|---|---|---|
| Cox1 | AF207823 | GGGAGTCCTTCTCCAATGTG | CATAAATGTGGCCGAGGTCT |
| Cox2 | AF207824 | ATGATCTACCCGCCTCACAC | AAAAGCAGCTCTGGGTCAAA |
| iNOS | X98196 | TGCGTTATGCCACCAACAATG | ACTCTCCAGGATGTTGTAG |
| Aggrecan | AF201722 | CAGGAGAAGAGATGCCAAC | CAGGTGATCCGAGGCTCC |
| β-actin | SSU07786 | TGCAGGTGACCATGGCC | CGGTAATGGAACACAACCCCT |

Table 1

FIG 11

| INGREDIENT | % by weight |
|---|---|
| New Zealand Green Lipped Mussel | 50.90 |
| Abalone | 16.98 |
| Honey flavoring | 7.47 |
| Shark Cartilage Powder | 21.23 |
| 'Constituent 4' | 6.67 |

Table 2

FIG 12

| Nutrient | | |
|---|---|---|
| Crude protein | min | 12.5% |
| Crude fat | min | 2.5% |
| Crude fiber | max | 8.5% |
| Sodium (Na) | actual | 0.3% |
| Calcium (Ca) | actual | 0.65% |
| Phosphorus (P) | actual | 0.55% |
| Copper (Cu) | actual | 30 mg/kg |
| Vitamin A | min | 4,550 I.U./kg |
| Vitamin $D_3$ | min | 840 I.U./kg |
| Vitamin E | min | 70 I.U./kg |

TABLE 3

FIG 13

NUTRACEUTICAL COMPOSITION AND METHODS OF USE

This application is a continuation-in-part of U.S. Utility patent Ser. No. 12/812,488, filed 12 Jul. 2010, which is a 371 National Stage Entry of International Application No. PCT/AU2008/001834 filed 12 Dec. 2008, which claims the priority to Australian Application No. 2007906771, filed on 12 Dec. 2007, wherein the specifications and contents of these applications are hereby incorporated herein by reference in their entirety.

BACKGROUND OF THE INVENTION

Field of the Invention

Embodiments of the invention relate generally to nutraceutical compositions and methods of administering them for the treatment of inflammation or inflammation associated disorders.

Embodiments of the invention also relate to nutraceutical compositions extracts from a plant capable of treating inflammation or inflammation associated disorders.

Description of the Related Art

In this specification, where a document, act or item of knowledge is referred to or discussed, this reference or discussion is not an admission that the document, act or item of knowledge or any combination thereof was at the priority date: part of common general knowledge, or known to be relevant to an attempt to solve any problem with which this specification is concerned.

The use of non-steroidal anti-inflammatory drugs (NSAID), such as aspirin and ibuprofen, for the treatment of pain, inflammation and fever is well known. Adverse reactions from such drugs are widespread and increasingly prevalent resulting in over 100,000 hospitalisations in the US in 2001. Some of the newer NSAID's have been shown to increase a patients risk of myocardial infarction by 80%.

Moreover, there have been a number of increased adverse drug reactions (ADR), particularly when the NSAID was taken in combination with a COX-2 inhibitor.

Some common gastrointestinal ADR's observed include, nausea, vomiting, dyspepsia, gastric ulceration and diarrhoea, other more severe ADR's have also been observed to include hypertension, interstitial nephritis, acute renal failure and photosensitivity.

NSAID's work primarily as a COX inhibitor, and certain NSAID's were developed as specific COX-1 or COX-2 inhibitors.

In 2004, the US FDA issued a public health advisory on the safety of Vioxx™, a selective COX-2 inhibitor, on the basis that there was an increase in cardiovascular events observed in those taking the drug.

In 2005, the US FDA issued an alert for practitioners in relation to the safety of the NSAID Celebrex™ again on the basis of the observed increase in cardiovascular events in patients taking the drug.

As a result of the above there has been a general reluctance to prescribe known NSAID's in many situations, or to prescribe reduced dosages in an attempt to combat the adverse side effects currently being observed.

NSAID's have long been used in the treatment of joint inflammation as a form of pain relief.

Shark cartilage provides significant improvement in joint health in an experimental model of immune-mediated arthritis (Pivnenko et al., 2005), and may improve sulfate uptake into new proteoglycan molecules.

Similarly, there is clinical evidence for the efficacy of perna mussel as a treatment for degenerative joint disease in dogs (Pollard et al., 2006; Bui and Bierer 2003). Likewise abalone has potential benefits in alleviating and treating joint disease. It has a high concentration of n-3 polyunsaturated fatty acids (Su and Antonas 2004) which are known to reduce the formation of inflammatory eicosanoids (Mesa Garcia et al., 2006) and at least in part account for the inhibition of nitric oxide production (Pearson et al., 2007). The latter being linked with chondroprotective and analgesic properties (Pearson et al., 2007).

BRIEF SUMMARY OF THE INVENTION

It is an object of the invention to provide a nutraceutical composition for the treatment of inflammation or inflammation associated disorders.

It is an object of the present invention to overcome, or at least substantially ameliorate, the disadvantages and shortcomings of the prior art.

Other objects and advantages of the present invention will become apparent from the following description, taking in connection with the accompanying drawings, wherein, by way of illustration and example, an embodiment of the present invention is disclosed.

In a first aspect of the invention there is a method of treating joint inflammation in a mammal in need thereof, the method including obtaining hydrolysed *Biota orientalis* seed oil and administering to the mammal a composition including an effective amount of the hydrolysed *Biota orientalis* seed oil to said mammal.

In preference, the composition inhibits Cox expression in said mammal, wherein said inhibiting comprises administering to said mammal said non-aqueous extract of said seed of said *Biota orientalis* plant in an effective amount to inhibit Cox expression.

In preference, the composition includes an additional extract selected from the group consisting of mussel extract, abalone extract or powder, shark cartilage powder or combinations thereof.

In preference, the composition includes a pharmaceutical carrier.

A further aspect of the invention is a method for treating joint inflammation in a mammal in need thereof, the method including obtaining hydrolysed *Biota orientalis* seed oil and administering to the mammal a composition including an effective amount of the hydrolysed *Biota orientalis* seed oil to said mammal, wherein said obtaining said hydrolysed *Biota orientalis* seed oil comprises adding *Biota orientalis* seed oil to an alkaline solution of about 1:2.9:1.4 (w/w) KOH:EtOH:cold water; neutralising said alkaline solution to a pH of about 4.5; and separating a non-aqueous phase to yield the hydrolysed *Biota orientalis* seed oil.

In a further aspect of the invention, although this should not be seen as limiting the invention in any way, there is provided a method of modulating inflammation in an organism, the method including administering to an organism a composition including a therapeutic amount of an extract from the plant *Biota orientalis*.

In a typical method, administering a composition a composition including a therapeutic amount of an extract from the plant *Biota orientalis* to an organism decreases inflammation in the organism.

In one embodiment, a composition for modulating inflammation including a *B. orientalis* extract as described herein further includes an additional extract such as mussel extract, abalone extract or powder, shark cartilage powder or combinations thereof.

In one embodiment, the *B. orientalis* extract can be produced from a simulated digest mimicking gastrointestinal functioning/processing.

In a further aspect of the invention there is a provided a method of inhibiting cox expression in an organism, the method including administering to an organism a therapeutic or prophylactic amount of an extract from the plant *Biota orientalis*.

In preference, the cox is cox 1.

In preference, the cox is cox 2.

In preference, the cox expression is inhibited by greater than 70% "(e.g., 75, 80, 85, 90, 95%)".

A further aspect of the invention resides in the provision of a method of inhibiting IL-1-induced iNOS expression in an organism, the method including administering to an organism a therapeutic or prophylactic amount of an extract from the plant *Biota orientalis*.

In yet a further form of the invention, there is a therapeutic composition including a synergistic combination of an extract from the plant *Biota orientalis*, with one or more of shark cartilage, *perna* mussel extract or powder and abalone extract or powder.

In a further embodiment, the composition comprises an extract from the plant *Biota orientalis* at a concentration of 5-30% by weight, shark cartilage at a concentration of 10-30% by weight, abalone extract at a concentration of 10-30% by weight, and mussel extract at a concentration of 40-60% by weight.

In yet a further form of the invention there is a use of a composition including at least one of the compounds selected from the group consisting of (9Z,13S,15Z)-12,13-epoxyoctadeca-9,11,15-trienoic acid, cis, cis, cis-9,12,15-octadecatrienoic acid (ALA), cis, cis, cis-6,9,12-octadecatrienoic acid (GLA), cis, cis-9,12-octadecadienoic acid and 9-Octadecenoic acid for the manufacture of a medicament for the therapeutic and/or prophylactic treatment of anti-inflammatory conditions.

In preference, the medicament includes an additional extract such as *perna* mussel extract, abalone extract or powder, shark cartilage powder or combinations thereof.

A further form of the invention resides in a method of treatment for anti-inflammatory conditions in a mammal, which includes administering to the mammal a therapeutically effective amount of a polyunsaturated fatty acid.

In preference, the polyunsaturated fatty acid is selected from the group of omega-3, omega-6, omega-9 and conjugated fatty acids or mixtures thereof.

In preference, the omega-3 fatty acid is selected from the group including: cis,cis,cis-7,10,13-hexadecatrienoic acid; cis,cis,cis-9,12,15-octadecatrienoic acid; cis,cis,cis-6,9,12,15-octadecatetrae-noic acid; cis,cis,cis-11,14,17-eicosatrienoic acid; cis,cis,cis,cis-8,11,14,17-eicosatetraenoic acid; cis,cis,cis,cis-5,8,11,14,17-eicosapentaenoic acid; cis,cis,cis,cis-7,10,13,16,19-docosapentaenoic acid; cis,cis,cis,cis,cis-4,7,10,13,16,19-docosahexaenoic acid; cis, cis,cis,cis-9,12,15, 18,21-tetracosapentaenoic acid; and cis, cis,cis,cis,cis-6,9,12,15,18,21-tetracosahexaenoic acid or mixtures thereof.

In preference, the omega-6 fatty acid is selected from the group including: cis,cis-9,12-octadecadienoic acid; cis,cis, cis-6,9,12-octadecatrienoic acid; cis,cis,cis-11,14-eicosadienoic acid; cis,cis,cis-8,11,14-eicosatrienoic acid; cis,cis,cis-5,8,11,14-eicosatetraenoic acid; cis,cis-13,16-docosadienoic acid; cis,cis,cis,cis-7,10,13,16-docosatetraenoic acid; and cis,cis,cis,cis,cis-4,7,10,13,16-docosa-pentaenoic acid or mixtures thereof.

In preference, the omega-9 fatty acid is selected from the group including: cis-9-octadecenoic acid; cis-11-eicosenoic acid; cis,cis,cis-5,8,11-eicosatrienoic acid; cis-13-docosenoic acid; and cis-15-tetracosenoic acid or mixtures thereof.

In preference, the conjugated fatty acid is selected from the group including: 9Z,11E-octadeca-9,11-dienoic acid; 10E,12Z-octadeca-9,11-dienoic acid; 8E,10E,12Z-octadecatrienoic acid; 8E,10E,12E-octadecatrienoic acid; 8E,10Z, 12E-octadecatrienoic acid; 9E,11E,13Z-octadeca-9,11,13-trienoic acid; 9E,11E,13E-octadeca-9,11,13-trienoic acid; 9Z,11Z,13E-octadeca-9,11,13-trienoic acid; 9Z,11E,13Z-octadeca-9,11,13-trienoic acid; 9E,11Z,15E-octadeca-9,11,15-trienoic acid; 9E,11Z,13Z,15E-octadeca-9,11,13,15-trienoic acid; trans,trans,trans,trans-octadeca-9,11,13,15-trienoic acid; (9Z,13S,15Z)-12,13-epoxyoctadeca-9,11,15-trienoic acid; and 5Z,8Z,10E,12E,14Z-eicosanoic acid or mixtures thereof.

In preference, the fatty acid(s) are/is in a form of a salt.

Another form of the invention resides in a pharmaceutical preparation anti-inflammatory conditions in a mammal, which includes a therapeutically effective amount of a polyunsaturated fatty acid.

The term "effective amount" as used herein refers to that amount of the extract that will contribute to the ability of the composition to treat joint inflammation.

BRIEF DESCRIPTION OF THE DRAWINGS

The above and other aspects, features and advantages of the invention will be more apparent from the following more particular description thereof, presented in conjunction with the following drawings wherein.

represents treatments significantly different from stimulated (A) or unstimulated (B) controls. Indo$_{sim}$, SEQ$_{sim}$ (both doses) and BO$_{sim}$ (0.18 mg/mL) resulted in significantly lower $PGE_2$ in stimulated explants compared with stimulated controls. Indo$_{sim}$ and SEQ$_{sim}$ lowered $PGE_2$ production in unstimulated explants relative to unstimulated controls.

Figure 6:
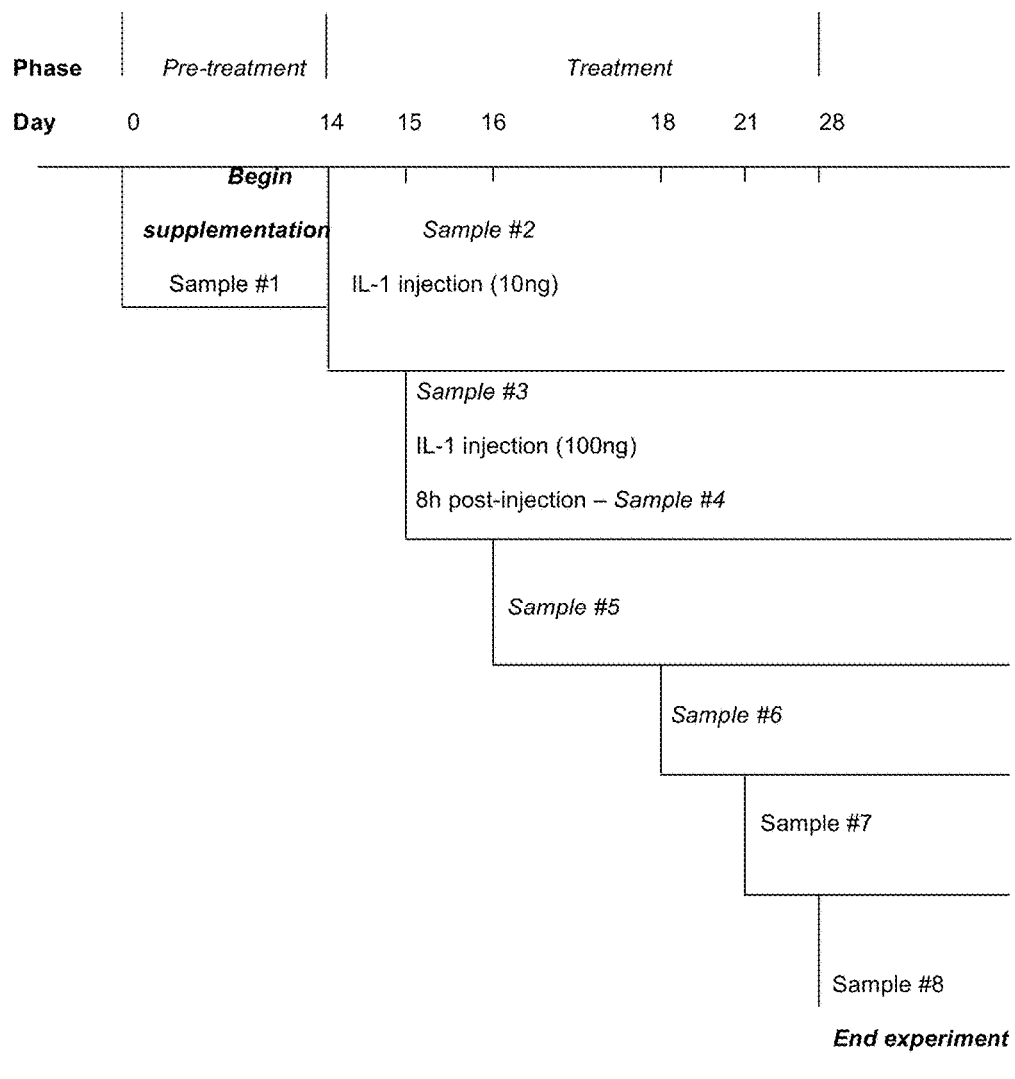

FIG. 6: Timeline of injections and sample collection; Sample collection consisted of synovial fluid arthrocentesis from left and right intercarpal joints, and jugular venous blood. Dietary supplementation began on day 0 and continued for the duration of the experiment.

Figure 7:
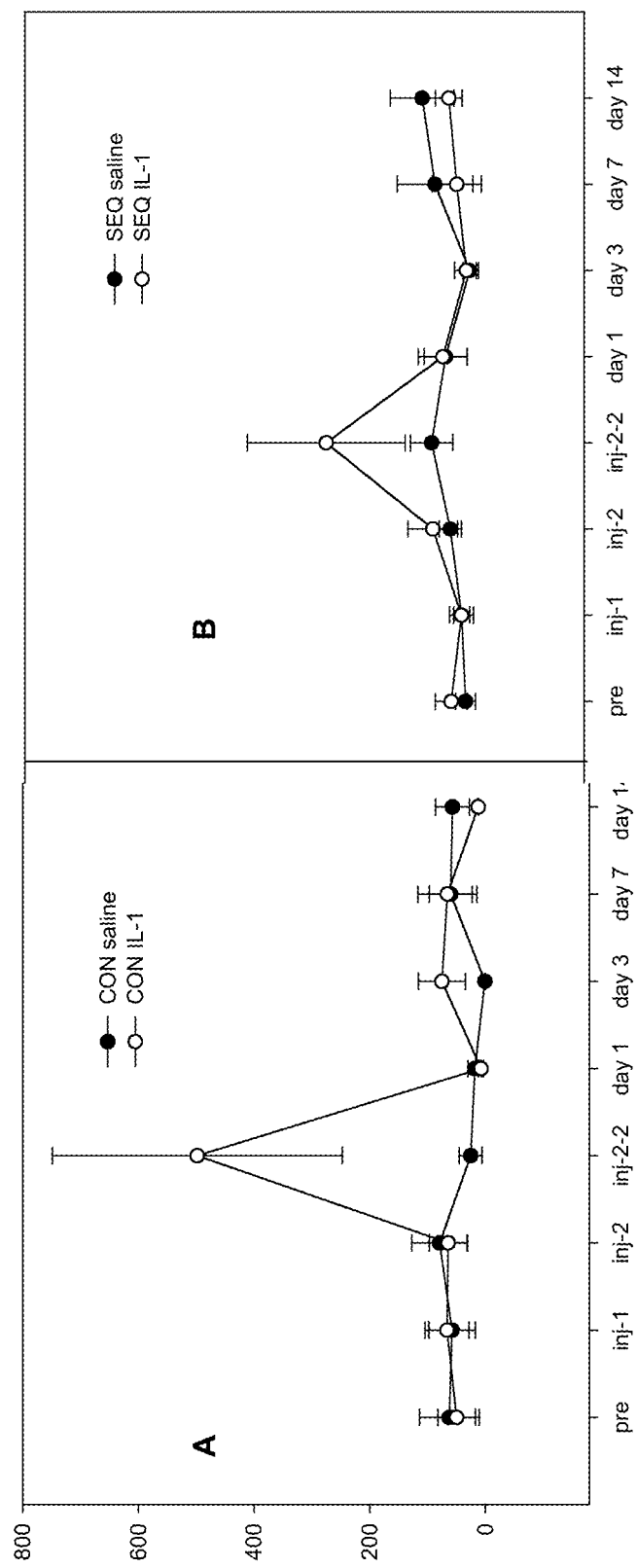

FIG. 7: Synovial fluid [$PGE_2$] from intercarpal joints of control horses injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 μL sterile saline) was injected into the intercarpal joint, and sterile saline (500 µL) was injected into the contralateral joint 14 days after commencement of supplementation (inj-1). A second intra-articular injection of IL-1 (100 ng in 500 µL sterile saline) or saline (500 µL) was injected the same joints 24 h later (inj-2). Approximately 1.5 mL synovial fluid was aspirated from the intercarpal joints on days pre (before commencement of supplementation), inj-1 and inj-2 (prior to injections), inj-2-2 (8 h after $2^{nd}$ IL-1 injection), and 1, 3, 7 and 14 days after $2^{nd}$ IL-1 injection. * denotes significant change from inj-1 within treatments. Letters denote significant differences between saline and IL-1 within treatments. Changes are significant when $p \leq 0.05$.

Figure 8:
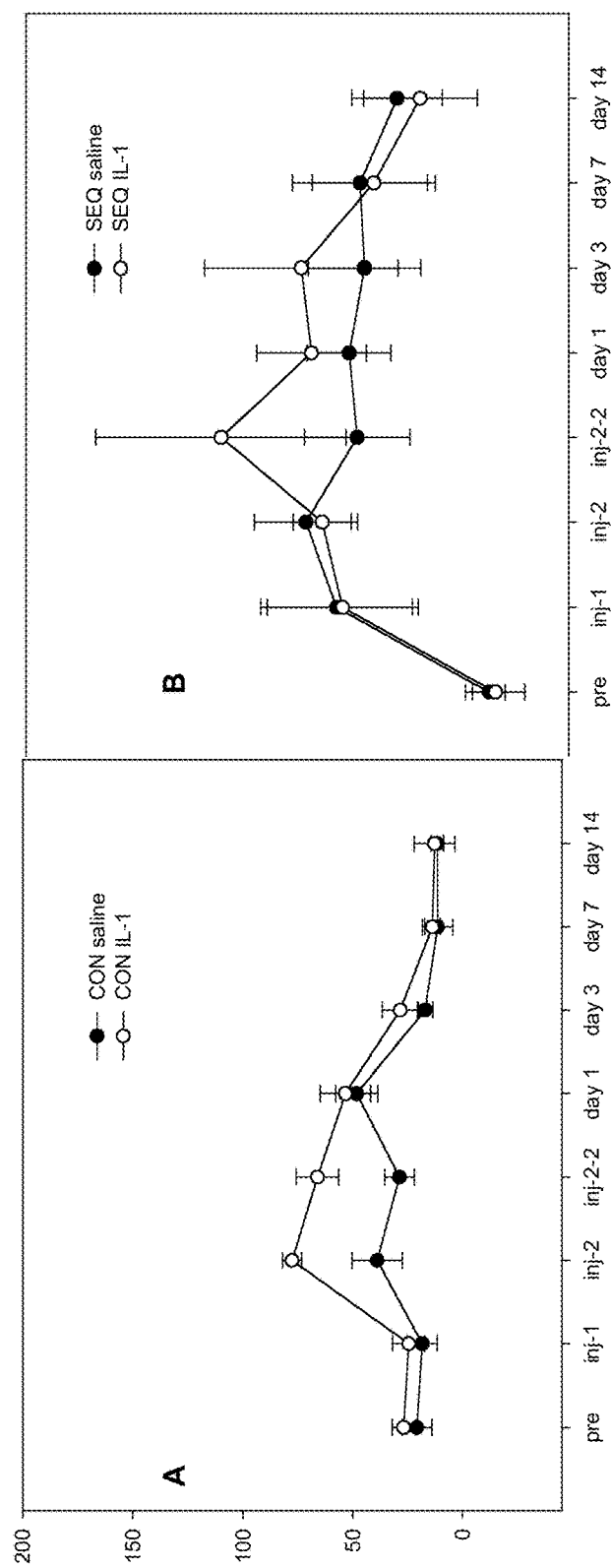

FIG. 8: Synovial fluid [GAG] from intercarpal joints injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 µL sterile saline) was injected into the intercarpal joint, and sterile saline (500 µL) was injected into the contralateral joint 14 days after commencement of supplementation (inj-1). A second intra-articular injection of IL-1 (100 ng in 500 µL sterile saline) or saline (500 µL) was injected the same joints 24 h later (inj-2). Approximately 1.5 mL synovial fluid was aspirated from the intercarpal joints on days pre (before commencement of supplementation), inj-1 and inj-2 (prior to injections), inj-2-2 (8 h after $2^{nd}$ IL-1 injection), and 1, 3, 7 and 14 days after $2^{nd}$ IL-1 injection. * denotes significant change from inj-1 within treatments. Letters denote significant difference between IL-1 and saline within treatments. SEQ horses had significantly higher synovial fluid [GAG] than CON horses. Differences were significant when $p \leq 0.05$.

Figure 9:
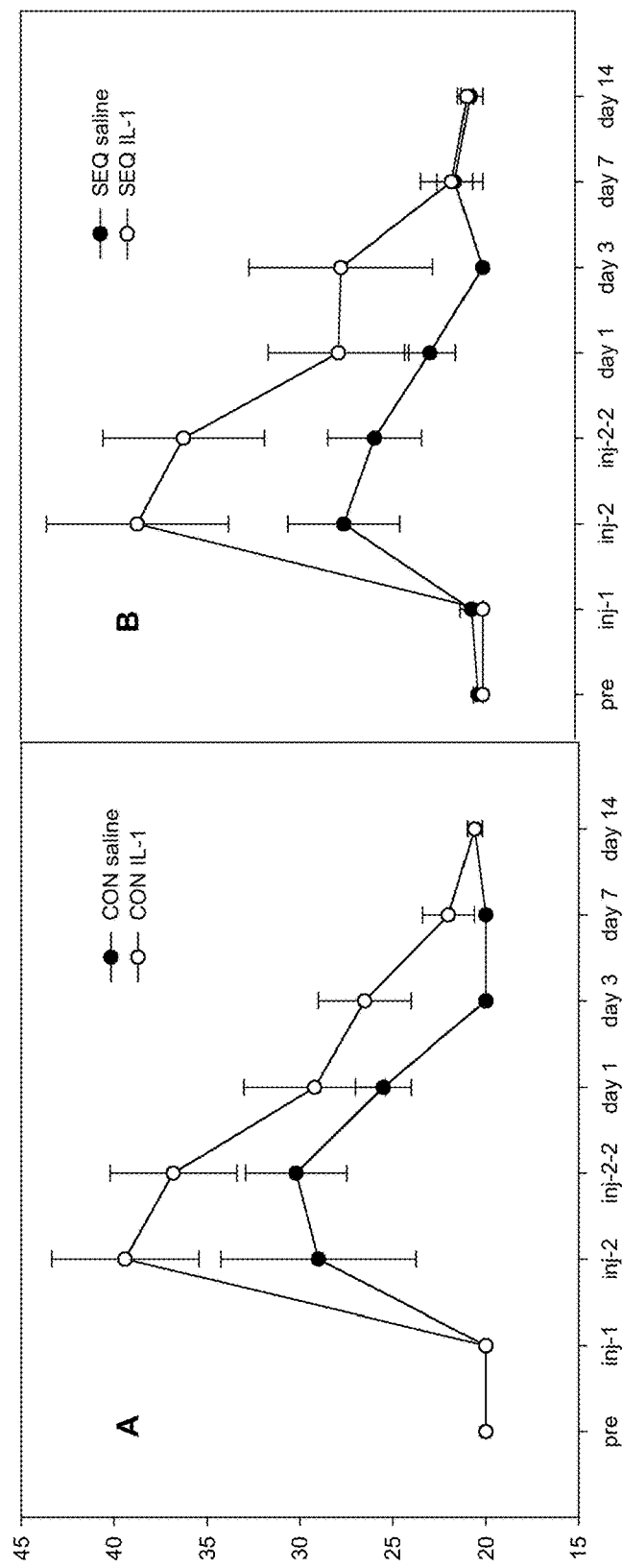

FIG. 9: Synovial fluid [protein] from intercarpal joints of control horses injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 µL sterile saline) was injected into the intercarpal joint, and sterile saline (500 µL) was injected into the contralateral joint 14 days after commencement of supplementation (inj-1). A second intra-articular injection of IL-1 (100 ng in 500 µL sterile saline) or saline (500 µL) was injected the same joints 24 h later (inj-2). Approximately 1.5 mL synovial fluid was aspirated from the intercarpal joints on days pre (before commencement of supplementation), inj-1 and inj-2 (prior to injections), inj-2-2 (8 h after $2^{nd}$ IL-1 injection), and 1, 3, 7 and 14 days after $2^{nd}$ IL-1 injection. * denotes significant change from inj-1 within treatments. Letters denote significant differences between saline and IL-1 within treatments. Differences were significant when $p \leq 0.05$.

Figure 10:
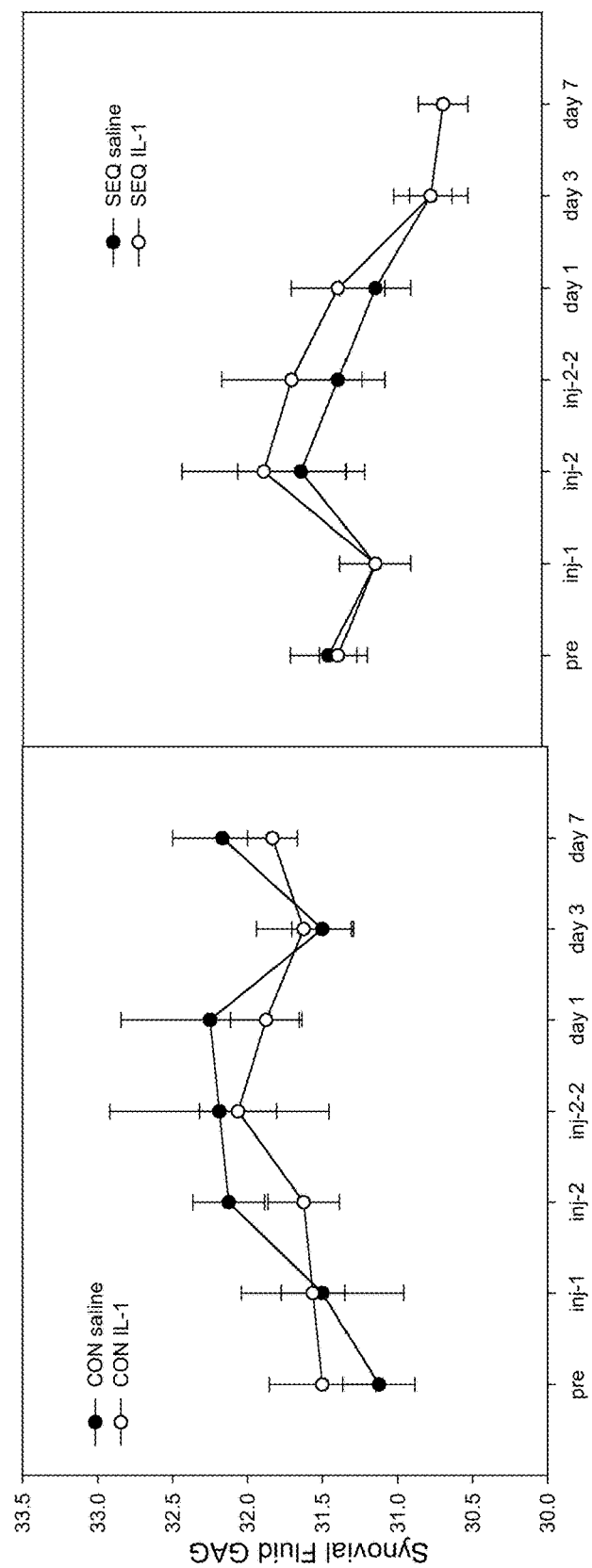

FIG. 10: Circumference of intercarpal joints injected with IL-1 (10 ng on inj-1, 100 ng on inj-2) or saline in CON (A) and SEQ (B) horses. Healthy horses received a diet containing placebo (CON) or Sasha's EQ (SEQ) for 28 days. Intra-articular IL-1 (10 ng in 500 µL sterile saline) was injected into the intercarpal joint, and sterile saline (500 µL) was injected into the contralateral joint 14 days after commencement of supplementation (inj-1). A second intra-articular injection of IL-1 (100 ng in 500 µL sterile saline) or saline (500 µL) was injected the same joints 24 h later (inj-2). Approximately 1.5 mL synovial fluid was aspirated from the intercarpal joints on days pre (before commencement of supplementation), inj-1 and inj-2 (prior to injections), inj-2-2 (8 h after $2^{nd}$ IL-1 injection), and 1, 3, 7 and 14 days after $2^{nd}$ IL-1 injection. * denotes significant change from inj-1 within treatments. Letters denote significant differences between saline and IL-1 within treatments. Joint circumference of IL-1-injected joints was significantly lower in SEQ horses than CON horses ($p<0.001$). Differences were significant when $p \leq 0.05$.

FIG. 11: Table 1 showing the primers for aggrecan and β-actin.

FIG. 12: Table 2 showing the composition of Sasha's EQ powder prepared by combining Abalone (AB), New Zealand Green Lipped Mussel (NZGLM), Shark cartilage (SC) and BO (Interpath Pty Ltd, Australia).

FIG. 13: Table 3 showing the nutrient composition of Sasha's EQ for feeding to horses.

Figure 14:
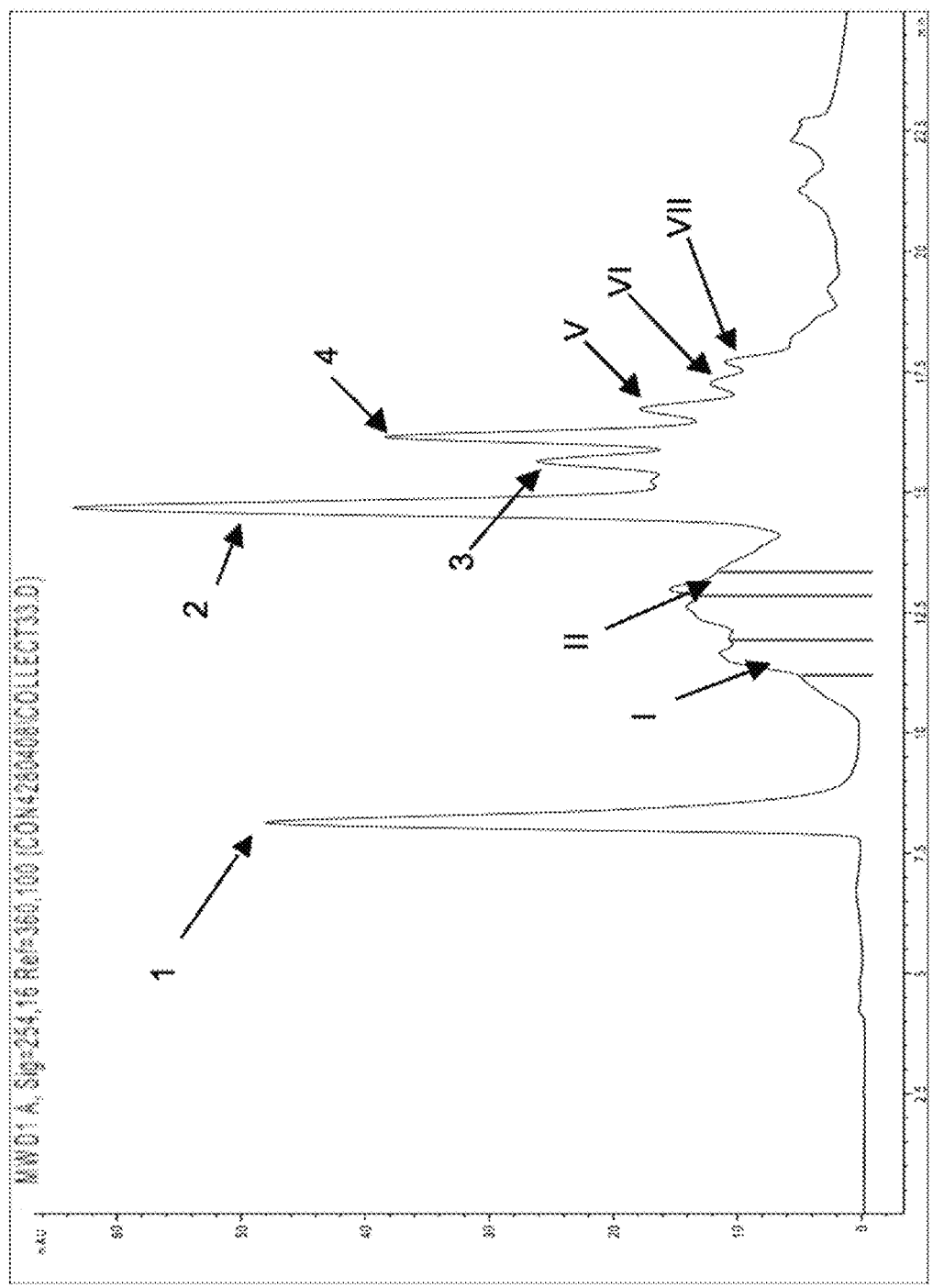

FIG. 14: Chromatographic spectrum of the extract of *Biota orientalis* oil.

Figure 15:
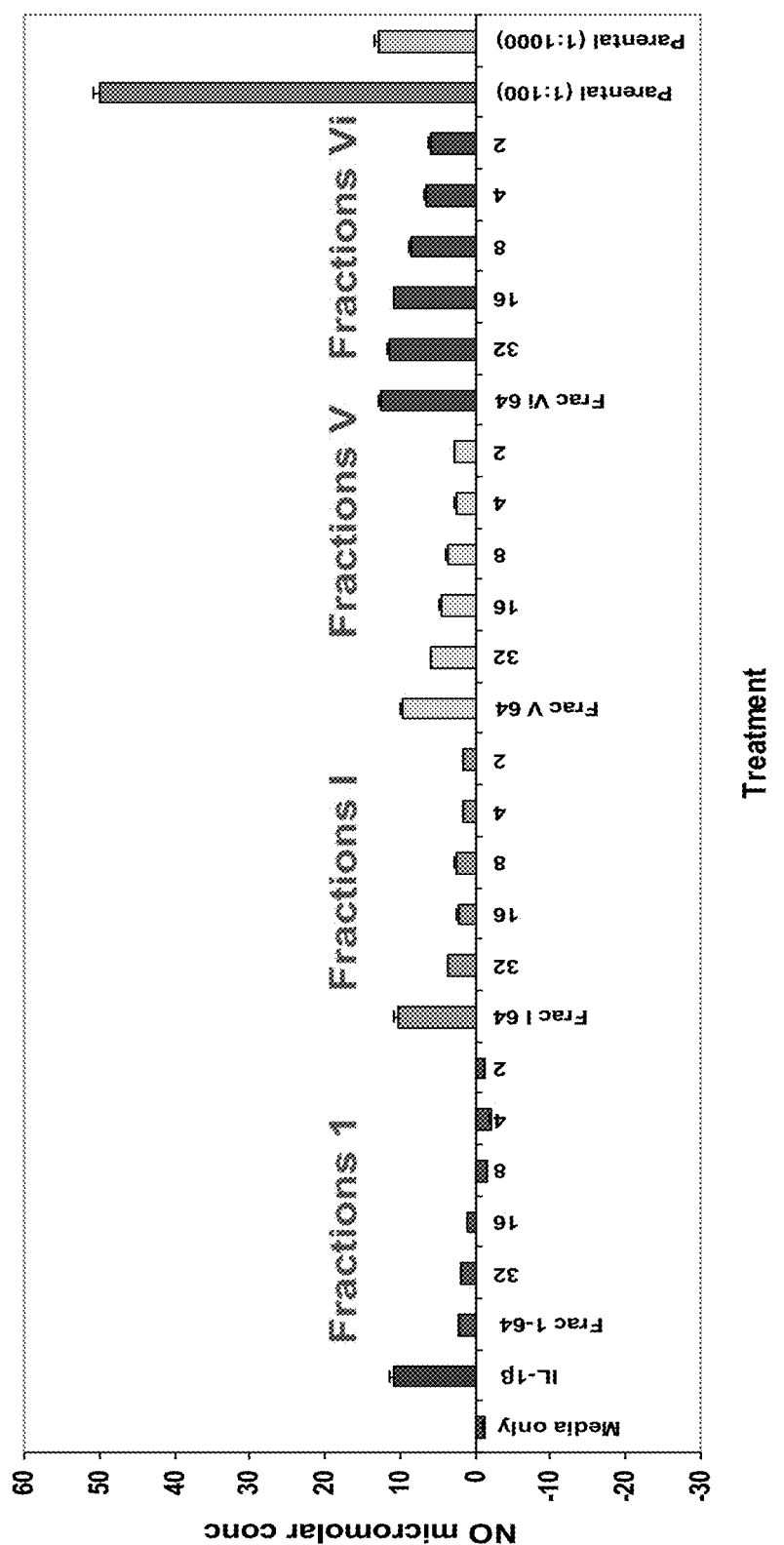

FIG. 15: Shows the concentration of NO of each of the isolated fractions in the cell culture assay.

Figure 16:
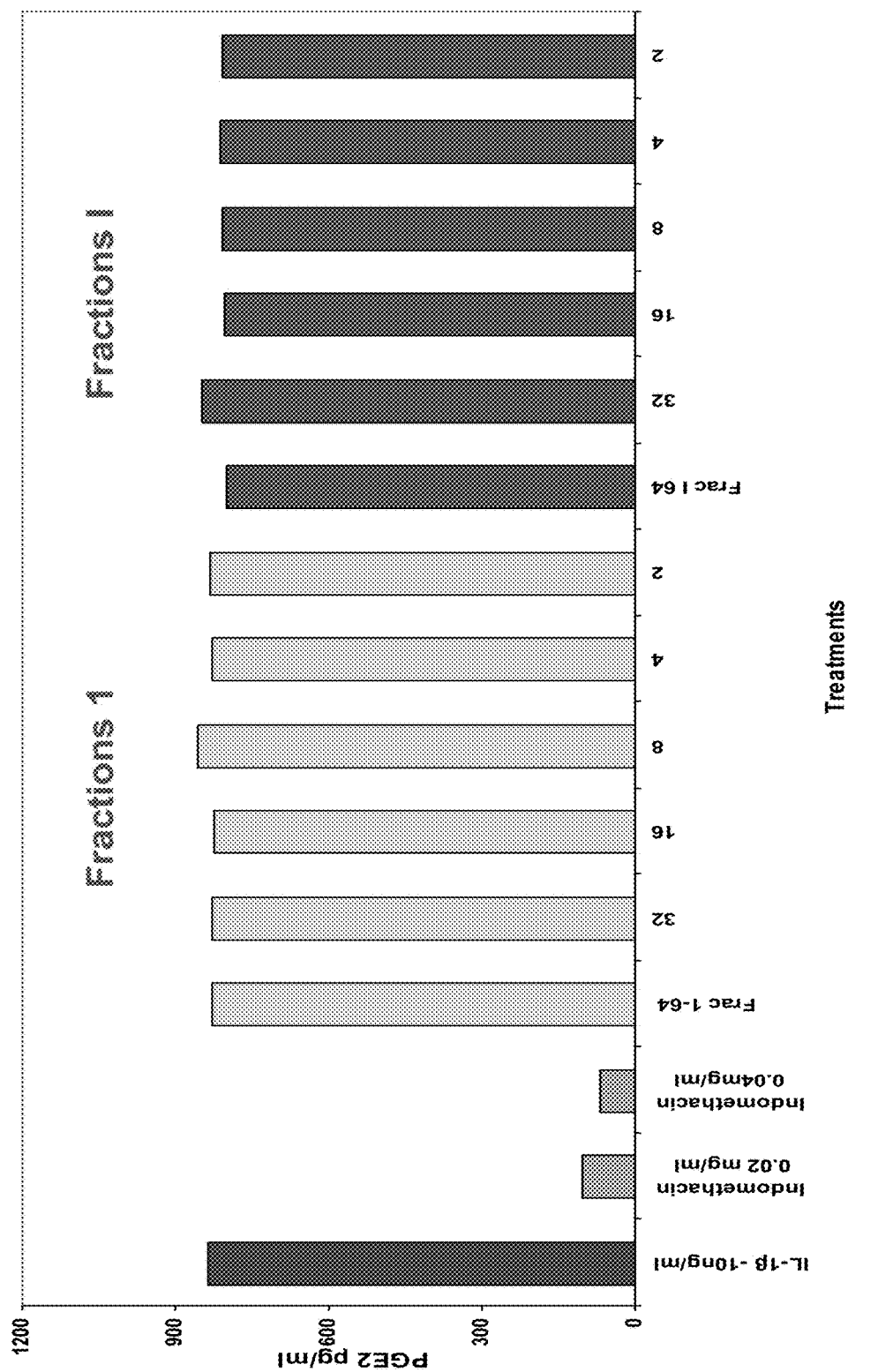

FIG. 16: Shows the induced PGE2 level of the isolated fractions Fr1 and FI.

Figure 17:
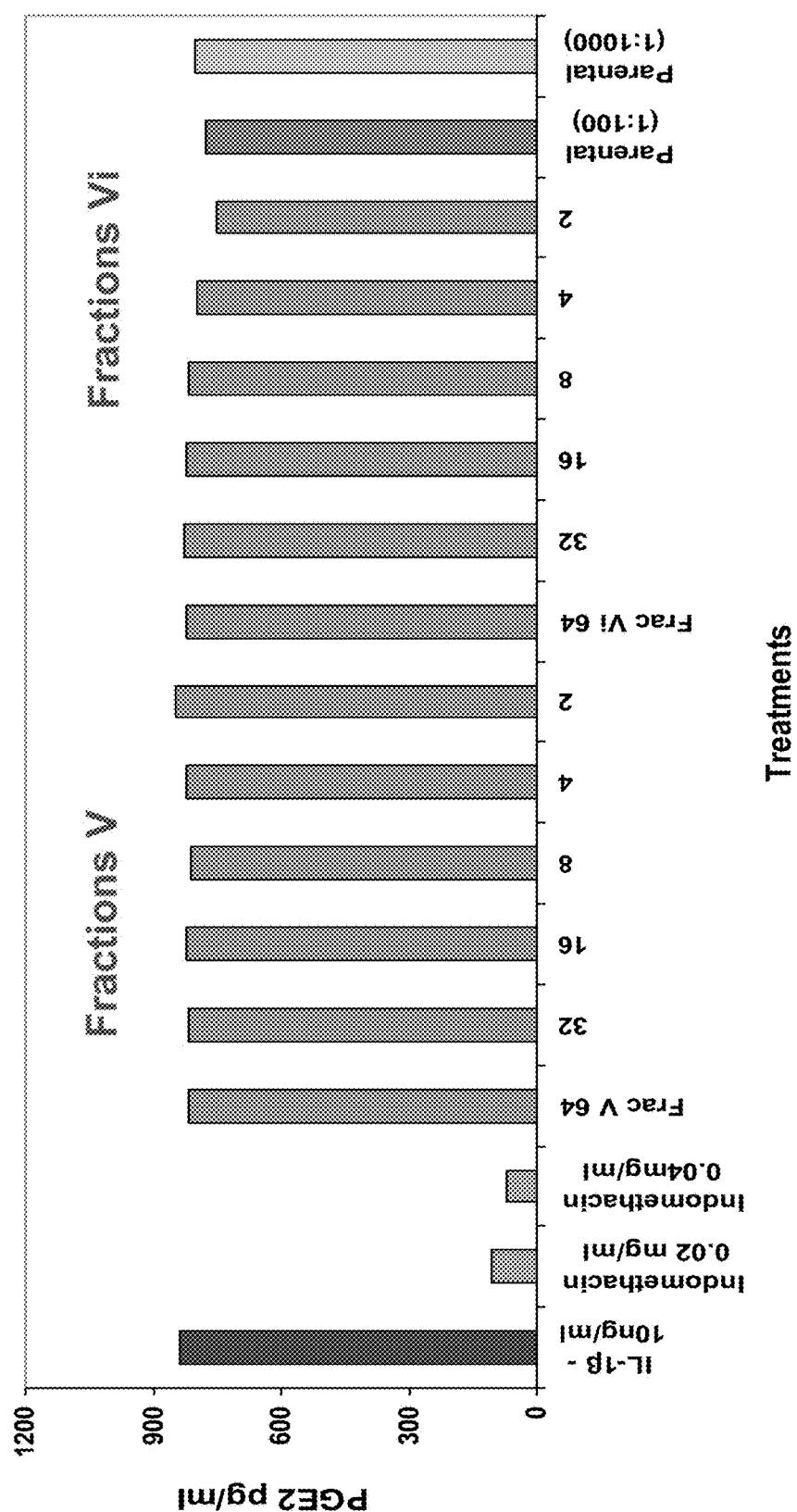

FIG. 17: Shows the induced PGE2 level of the isolated fractions FV and Vi

Figure 18:
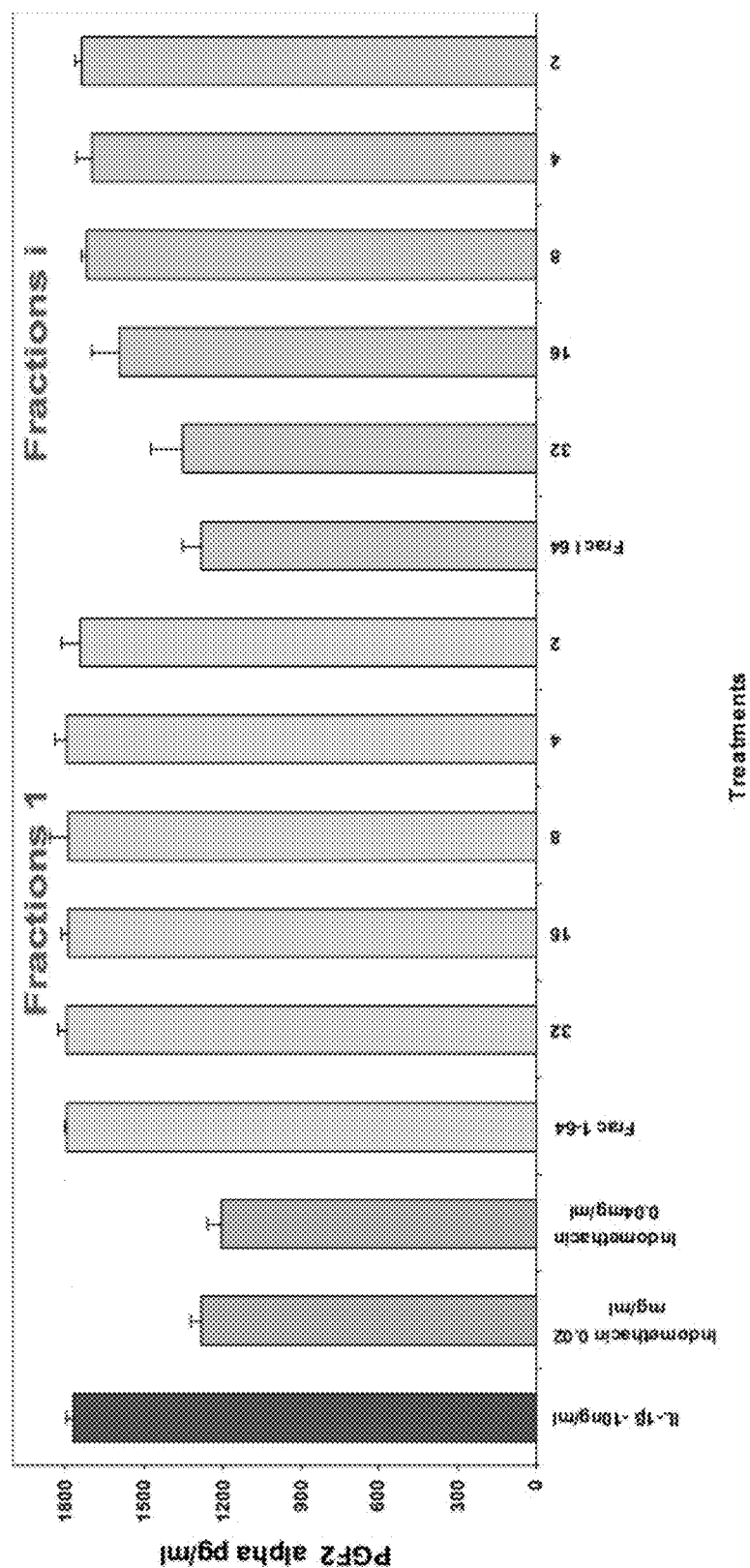

FIG. 18: Shows the reduction of IL-1β induced PGF2α levels on fractions Fr1 and Fri.

Figure 19:
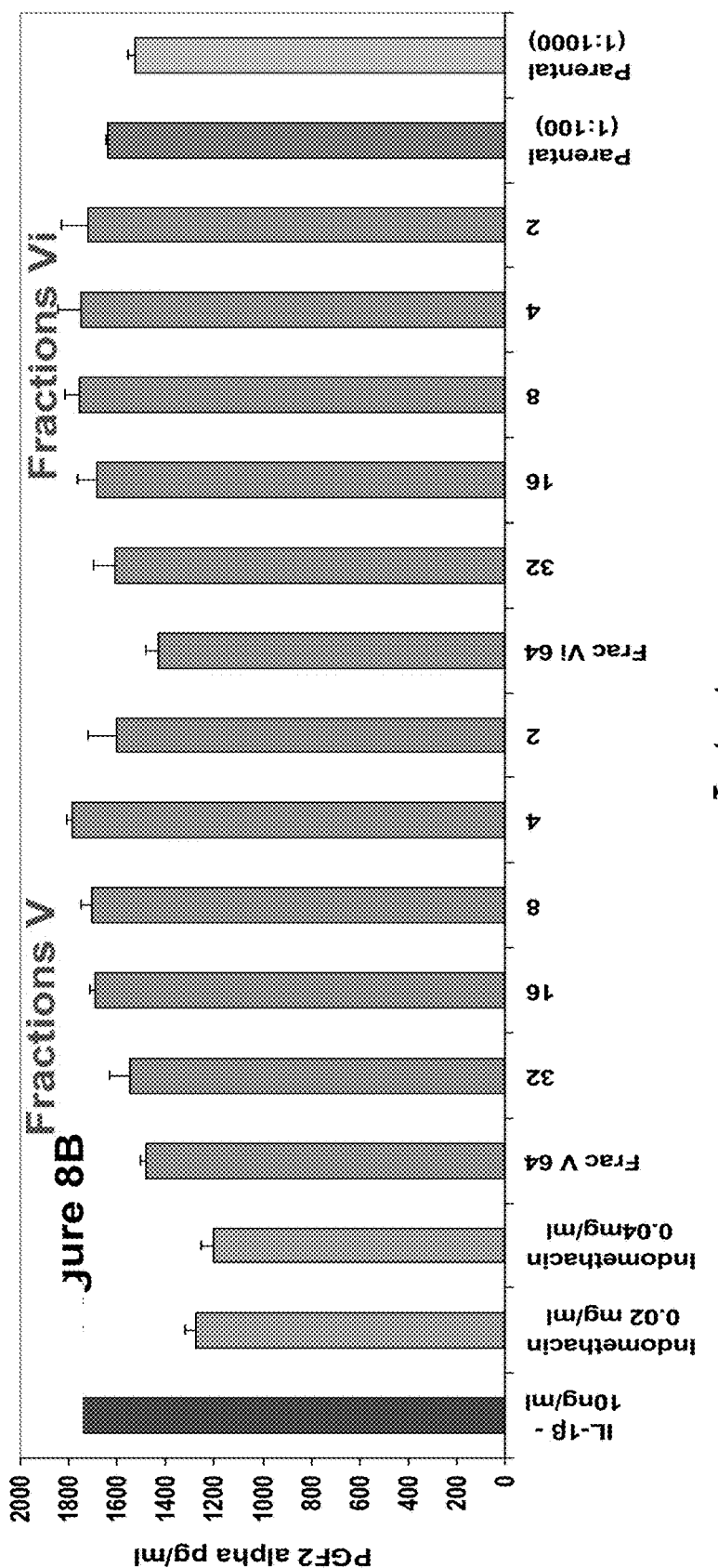

FIG. 19: Shows the reduction of IL-1β induced PGF2α levels on fractions FrV and FrVi.

DETAILED DESCRIPTION OF THE INVENTION

To facilitate an understanding of the invention various terms and abbreviations are used and defined below:

"SEQ" means a blend of New Zealand Green Lipped Mussel, abalone, shark cartilage powder and *Biota* oil.

"BO" means "*Biota* oil" being a hydrolysed extract of the seeds of the plant *Biota orientalis*. The crude *Biota* oil is hydrolysed to provide the *Biota* oil in the free fatty acid form.

"NZGLM" means New Zealand Green Lipped Mussel.

"sim" means a simulated digest or simulated digestion.

"COX" or "cox" means the enzyme cyclooxygenase.

"iNOS" means inducible nitric oxide (NO) synthase.

*Biota* is an herb native to Western China and North Korea and is known by a number of other names, such as *Thuja orientalis, Platycladus stricta*, and *Platycladus orientalis*.

Preparation of Hydrolysed *Biota orientalis* (BO) Seed Extract (Ex

| | |
|---|---|
| *Biota orientalis* (BO) seed extract (oil) | 60 kg |
| Ethanol | 44.4 kg |
| Cold water | 21 kg |
| Potassium hydroxide (KOH) | 15 kg |

Hydrolysis: KOH is dissolved in a mixture of cold water and ethanol (1:2.9:1.4 (w/w) KOH:EtOH:cold water), ensuring that the temperature of the solution is maintained at around 40° C. Once all the KOH is fully dissolved, check temperature to ensure that it is approximately 40° C. and slowly add the BO seed oil in 10 kg amounts taking care to monitor any increases in temperature and if required adding portions of cold water to ensure that the reaction solution temperature is maintained at around 40° C. under an inert atmosphere ($N_2$). Continue until all BO seed oil has been added. Continue stirring reaction mixture for 1.5 hrs adding whilst maintaining temperature of mixture at around 40° C.

Neutralisation: Prepare a solution of 36% sulphuric acid (49 kg) and ensuring the reaction mixture is approximately 40° C. slowly add 15 kg the 36% sulphuric acid solution and check pH. Continue adding portions of the 36% sulphuric acid solution and monitoring the pH until the pH is approximately 6. Continue mixing adding smaller portions (25-50 ml) of 36% sulphuric acid until the pH is approximately in the range of 4.5-4.6.

Extraction: drain the aqueous phase (water/ethanol) from the reaction mixture and wash the non-aqueous phase with warm (40° C. water), retain the non-aqueous phase and repeat washing step if required. Separate again the non-aqueous phase which is the hydrolysed BO seed oil.

An alternative hydrolysis process is as follows:

Enzyme hydrolysis: 80% by total weight of BO seed oil is mixed together with 20% by total weight of water. Lipozyme® RM IM (2% of the weight of BO seed oil) is then added. The mixture is stirred and heated until it reaches 45° C. The temperature of 45° C. and stirring are then maintained for 6 hours.

Separation and drying: After 6 hours the reaction mixture is filtered to remove any insoluble material and to recover the immobilised enzyme. The oil phase is separated either by gravity settling and decanting or by centrifugal separation. Optionally additional warm water can be mixed with the oil before separation to remove additional water soluble components from the oil. The separated oil phase is then evaporated under vacuum to remove remaining moisture.

Lipozyme® RM IM is a commercial immobilised lipase from *Rhizomucor miehei*. Other lipases are also suitable to act as the hydrolysis biocatalyst.

Simulated digests of shark cartilage, NZGLM and abalone have been previously reported to have anti-inflammatory effects in a cartilage explant model of arthritis by reducing $PGE_2$, GAG and/or nitric oxide (Pearson et al., 2007).

The following data reports alterations in gene expression associated with conditioning cartilage explants with simulated digests of the combination of all four constituents (SEQ; $SEQ_{sim}$), and to characterize their effects on IL-1-induced $PGE_2$, GAG, NO, cell viability, and genetic expression of cox 1, cox 2, iNOS and aggrecan.

Methods

Explant Cultures

Front legs of market weight pigs (5-7 months old, 200-250 lbs) were obtained from a local abattoir. Legs were chilled on crushed ice until dissection. Using aseptic technique, the intercarpal joint was opened and the cartilage surfaces exposed. A 4 mm dermal biopsy punch was used to take explants (~0.5 mm thickness; 11-15 mg/explant) of healthy cartilage from the weight-bearing region of both articulating surfaces of the intercarpal joint. Cartilage pieces were washed 3 times in DMEM supplemented with $NaHCO_3$. Two cartilage discs were placed into each well of 24-well tissue culture plates containing DMEM supplemented with amino acids, sodium selenite, manganese sulfate, $NaHCO_3$ and ascorbic acid (TCM—tissue culture medium). Plates were incubated at 37° C., 7% $CO_2$ in a humidified atmosphere for up to 144 h. Every 24 h media was completely aspirated into 1 mL microcentrifuge tubes and immediately replaced with control, conditioned and/or stimulated media (described below) before being returned to the incubator. The collected media was stored at −80° C. until analysis. Cartilage was harvested at the end of each experiment with one explant per well stained for cytotoxicity and the remaining cartilage immediately frozen at −80° C.

Simulated Digestion and Ultrafiltration

A simulated digestion procedure was developed to mimic the gastrointestinal processing of ingested dietary supplements. This type of approach has previously been used to improve the bio-assessment of putative nutraceuticals (Rininger et al., 2000; Pearson et al., 2007).

Simulated digests were prepared using SEQ (0.85 g), BO [2.5 mL (0.85 g)] and indo (0.074 g—a positive anti-inflammatory control). Each test substance was individually suspended in 35 mL of simulated gastric fluid (37 mM NaCl, 0.03N HCl, 3.2 mg/mL pepsin), and shaken at 37° C. for 2 h (Rininger et al., 2000). After this, solution acidity was neutralized by adding an equinormal volume of 2.2 N NaOH (1.15 mL). To this was added 36.15 mL of simulated intestinal fluid (Rininger et al., 2000-30 mM $K_2HPO_4$, 160 mM $NaH_2PO_4$; 20 mg/mL pancreatin; pH adjusted to 7.4) and the resultant mixture shaken in a 37° C. incubator for a further 2 h. A "blank" was prepared using identical methodology but without including any test substance. Appropriate volumes of gastric and intestinal fluid were derived from those approximated in a human stomach (Marciani et al., 2005).

Upon completion of the 4-hour incubation, simulated digests of SEQ ($SEQ_{sim}$) BO ($BO_{sim}$) and indomethacin ($indo_{sim}$) were centrifuged at 3,000×g for 25 min at 4° C. The supernatant was decanted and centrifuged a second time at 3,000×g for 15 min at 4° C. The resulting supernatant was warmed to room temperature and filtered (0.22 µm) to remove particulates. This filtrate was further fractioned with an ultrafiltration centrifuge unit with a 50 kDa molecular weight cut-off, (AmiconUltra, Millipore, Mississauga ON), spinning at 3,000×g for 25 min (room temperature). Filtered simulated digest was stored at 4° C. until use for a maximum of 7 days.

Effect of $SEQ_{sim}$ and $BO_{sim}$ on IL-1-Induced Inflammation $SEQ_{sim}$ was prepared as explained above. Explants from 12 pigs were prepared as previously described, and maintained in unconditioned media for the initial 24 h. At 24 hours post-culture, $SEQ_{sim}$, $BO_{sim}$ (0, 0.06 or 0.18 mg/mL) or $indo_{sim}$ (0.02 mg/mL) was added to TCM (conditioned media). Conditioned media was refreshed every 24 hours for the duration of the experiment. At 72 hours post-culture, and every 24 hours thereafter, explants were stimulated with IL-1 (0 or 10 ng/mL; Medicorp, Montreal, Quebec; Cat. #PHC0813). Explants from each animal were exposed to each treatment in duplicate. Explants were cultured for a total of 120 h. Media was analyzed for [$PGE_2$], [GAG], [NO]. One explant per treatment was collected into sterile phosphate buffered saline (PBS) and immediately stained for cell viability (see below). The second explant was frozen at −80° C. for RNA extraction (see below).

$PGE_2$ Analysis:

$PGE_2$ concentration of TCM was determined using a commercially available $PGE_2$ ELISA kit (The kit has 7% cross-reactivity with $PGE_1$) (Amershan, Baie D'Urfé, Québec). Plates were read using a Victor 3 microplate reader (Perkin Elmer, Woodbridge ON) with absorbance set at 405 nm. $PGE_2$ standard curves were developed for each plate, and a best-fit $3^{rd}$ order polynomial equation with $R^2 \geq 0.99$ was used to calculate $PGE_2$ concentrations for standards and samples from each plate.

NO Analysis:

NO concentration of tissue culture media was determined by the Griess Reaction (Shen et al., 2005). Plates were read using a Victor 3 microplate reader with absorbance set at 530 nm. Sodium nitrite standard curves were developed for each plate, and a best-fit linear regression equation with $R^2 \geq 0.99$ was used to calculate NO concentrations, which were compared with the nitrite standard.

Isolation of Total RNA and Synthesis of cDNA

Total RNA was extracted from cartilage explants using a modified TRIzol procedure (Chan et al., 2005). Frozen cartilage from each animal was pooled according to conditioning and stimulation, and homogenized in Tri-Reagent (100 mg tissue/mL; Sigma, Mississauga ON). Chloroform was added to extract RNA followed by vigorous agitation and 2-min incubation at room temperature. Sample was then centrifuged (12,000×g, 15 min) and RNA was precipitated with an equal volume of 70% ethanol (DEPC). RNA precipitate was applied to an RNeasy mini column (Qiagen, Valencia Calif., USA) and RNA was purified according to manufacturer instructions.

For each pooled sample, 1 µg total RNA was converted to single stranded cDNA using Moloney Murine Leukemia Virus (MMLV) reverse transcriptase (Invitrogen, Burlington ON) according to manufacturer instructions. Single-strand cDNA was quantified by UV spectrophotometry and diluted with DEPC-$H_2O$ to a final concentration of 10 ng/µL.

Quantitative Real Time RT-PCR

Primers for porcine iNOS (Granja et al., 2006), Cox1/2 (Blitek et al., 2006), aggrecan (Fehrenbacher et al., 2003) and β-actin (housekeeping gene; Nishimoto et al., 2005) (Table 1) were prepared (Laboratory Services Division, University of Guelph) and stored at −20° C. until use. Cartilage samples from $SEQ_{sim}$ and $BO_{sim}$ were evaluated for changes in gene expression, together with cartilage cultured under identical conditions previously with the other 3 components of SEQ (see Pearson et al., 2007 for detailed culture conditions). Twenty five microliter PCR reactions were performed in triplicate using an ABI Prism 7000 sequence detection system (Perkin-Elmer). Amplification of 50 ng of each cDNA sample was detected using SYBR-Rox (Invitrogen, Burlington ON) and compared to a standard curve of pooled cDNA containing equal amounts of cDNA from each sample. A 1.5% agarose electrophoresis gel was used to confirm PCR products. Expression of each gene of interest (G) in each sample was compared to amplification of β-actin (β), and calibrated to unstimulated control explants (ie. fold change for calibrator=1). Fold change in expression ($\Delta G/\Delta \beta$) is presented in arbitrary units.

Cytotoxicity Staining

Cell viability was determined using a commercially available cell viability staining kit (Invitrogen; Burlington ON) (Pearson et al., 2007). Briefly, explants were washed in 500 uL PBS and placed into a 96-well microtitre plate (one explant per well), and were incubated in 200 uL of stock stain (4 µM C-AM; 8 µM EthD-1) for one hour at room temperature. The plate was read from the bottom of each well using 10 horizontal steps, 3 vertical steps, and a 0.1 mm displacement. C-AM and EthD-1 fluorescence in live and killed explants were obtained with excitation/emission filters of 485/530 nm and 530/685 nm, respectively.

Data Analysis

Data from analysis of tissue culture media and viability are presented as means±standard error. Means of replicates from each treatment/animal were analyzed using two-way repeated measures analysis of variance comparing each treatment with unconditioned controls and indomethacin-conditioned controls. Viability data were analyzed using the Student's t-test, individually comparing stimulated controls with all other treatments. When a significant F-ratio was obtained, the Holm-Sidak post-hoc test was used to identify significant differences between treatment and/or time. Significance was accepted if $p \leq 0.05$.

Due to low cellularity of cartilage explants, it was necessary to pool RNA from explants exposed to the same conditioning and stimulation in order to extract sufficient RNA for a reverse transcription reaction. Thus, PCR data are presented in the text as a mean change in gene expression (calibrated to controls) relative to β-actin±coefficient of variation for the assay. A calibrated fold expression change ≥2 is considered to be biologically relevant (Yang et al., 2002; Schena et al., 1995) and are discussed in the text as significant differences.

Results

PCR

Figure 1:
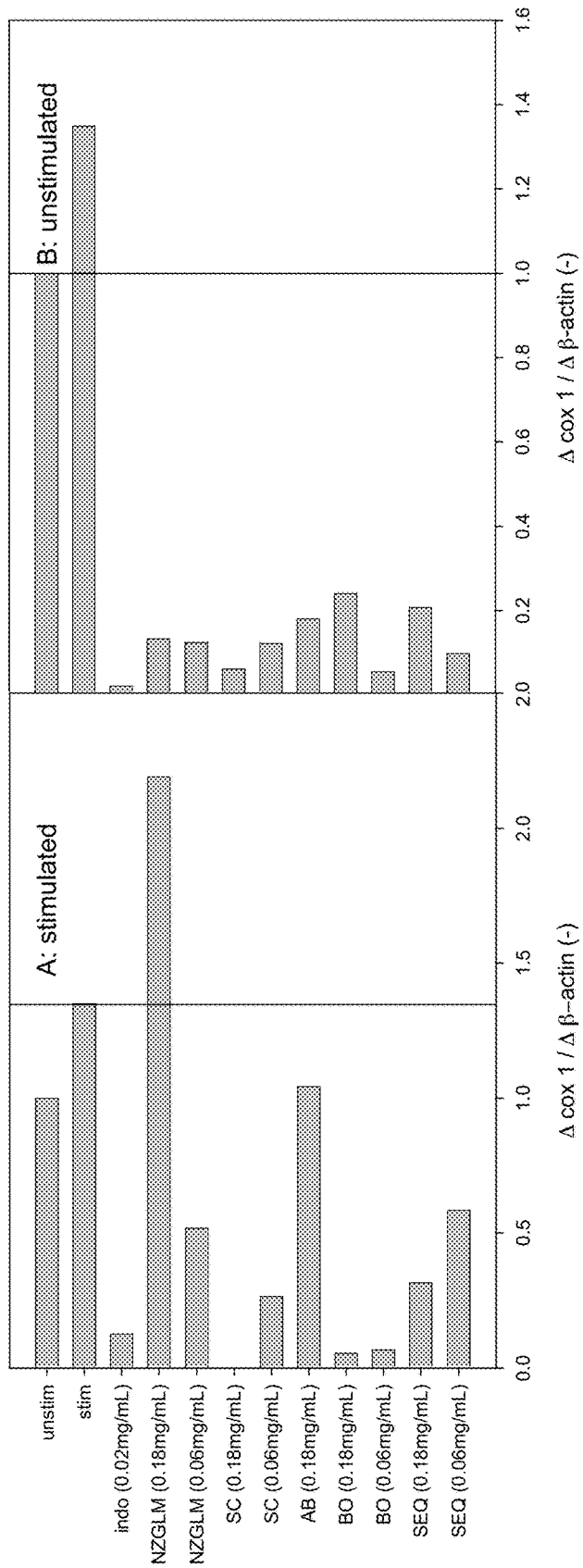
FIG. 1: Relative expression of cox 1 RNA in IL-1 stimulated (A) and unstimulated (B) cartilage explants.

Cox 1 (FIGS. 1, A and B): IL-1 stimulation of control explants resulted in a 35% increase in cox 1 expression compared with unstimulated controls. Cox 1 expression was decreased by exposure to $indo_{sim}$ by 98 and 91.5% in unstimulated and stimulated explants, respectively.

All constituents of SEQ reduced cox 1 expression in unstimulated explants (range: 76-95% inhibition). Importantly, it was observed that $BO_{sim}$ (0.06 mg/mL) was the most effective cox 1 inhibitor, reducing cox 1 expression by 95% in both unstimulated and stimulated explants.

In addition, it was observed that $SEQ_{sim}$ (0.06 and 0.18 mg/mL) reduced cox 1 expression in unstimulated explants by 90 and 80%, respectively. In IL-1 stimulated explants, $SEQ_{sim}$ (0.06 and 0.18 mg/mL) inhibited cox 1 expression by 57 and 76%, respectively. The least effective cox 1 inhibitor in IL-1-stimulated explants was NZGLM (0.18 mg/mL), which increased cox 1 expression by 62%.

Fold change in cox 1 for all samples was >2 and therefore not considered significant.

Figure 2:
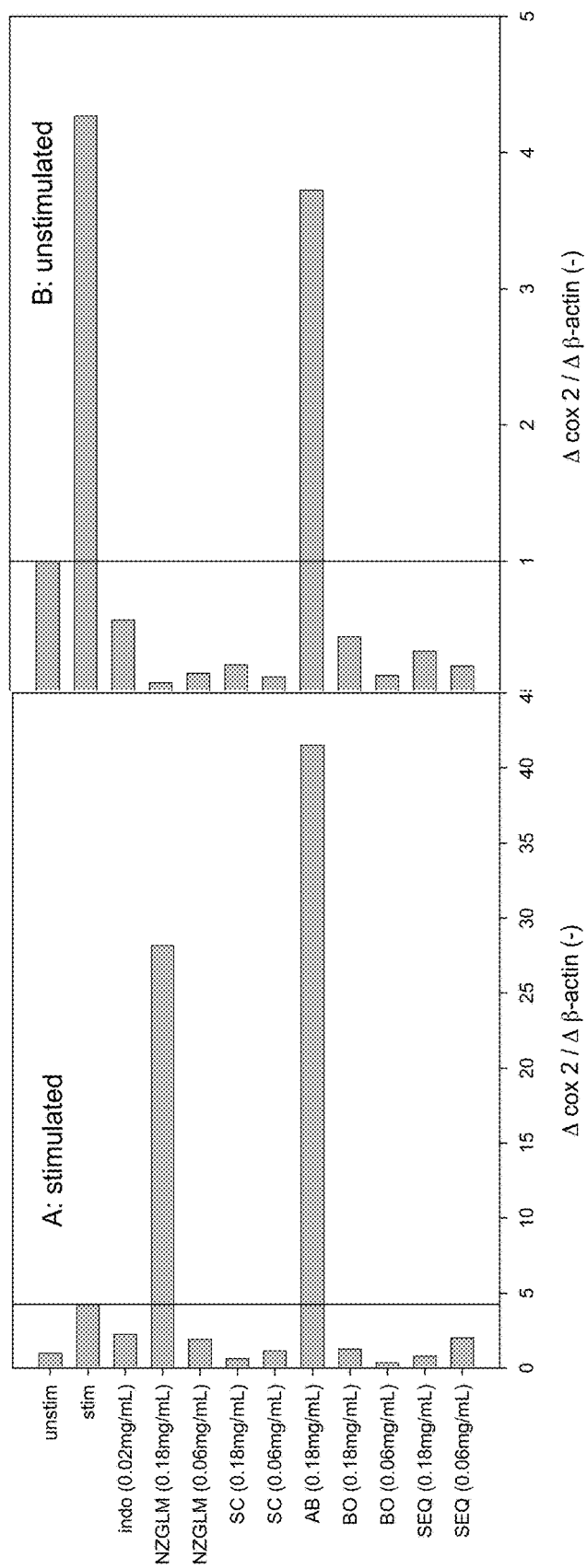
FIG. 2: Relative expression of cox 2 RNA in IL-1 stimulated (A) and unstimulated (B) cartilage explants.

Cox 2 (FIGS. 2, A and B): Stimulation of control explants resulted in a significant 4.3-fold increase in cox 2 expression. $Indo_{sim}$ reduced expression of cox 2 by 44 and 47% in unstimulated and stimulated explants, respectively. Fold increase in cox 2 for $indo_{sim}$-conditioned, IL-1-stimulated explants was significant (2.3).

Abalone (0.18 mg/mL) significantly increased cox 2 expression in unstimulated explants, showing similar effect on cox 2 (3.7-fold) as IL-1. All other constituents decreased Cox 2 expression in unstimulated explants (range: 56-90%).

Figure 3:
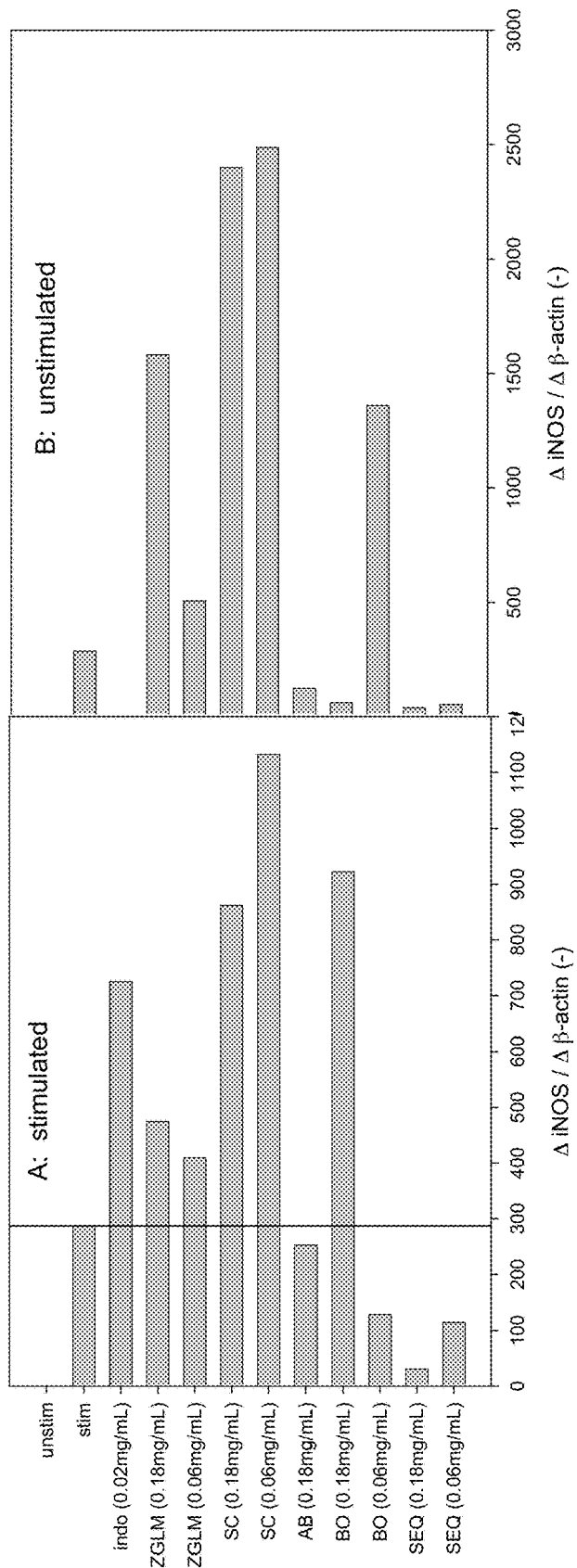
FIG. 3: Relative expression of iNOS RNA in IL-1 stimulated (A) and unstimulated (B) cartilage explants.

IL-1-stimulation resulted in a significant increase in cox 2 expression in those explants conditioned with $indo_{sim}$ (2.3-fold), $SEQ_{sim}$ (0.06 mg/mL; 2.0-fold), $NZGLM_{sim}$ (0.18 mg/mL; 28.2-fold), and $AB_{sim}$ (0.18 mg/mL; 41.5-fold). All other constituents prevented a significant increase in IL-1-induced cox 2 expression; the most effective inhibitor was $BO_{sim}$ (0.06 mg/mL) which inhibited cox 2 expression by 92%.

iNOS (FIGS. 3, A and B): Stimulation of control explants by IL-1 resulted in a 287-fold increase in iNOS expression. $Indo_{sim}$ conditioning had no effect on iNOS in unstimulated explants. In IL-1-stimulated explants, $indo_{sim}$ conditioning augmented the effect of IL-1 on iNOS expression (725-fold increase).

SEQ and all of its individual constituents significantly increased iNOS expression in unstimulated explants (range: 39-2486-fold increase). IL-1-stimulation resulted in a significant increase in iNOS expression in all conditioned explants. However, compared with IL-1-stimulated controls, iNOS was significantly inhibited by both doses of $SEQ_{sim}$ in a dose-dependent manner (60 and 89% inhibition for 0.06 and 0.18 mg/mL, respectively). $BO_{sim}$ (0.06 mg/mL) and $AB_{sim}$ (0.18 mg/mL) also significantly inhibited IL-1-induced iNOS expression by 55 and 12%, respectively.

Figure 4:
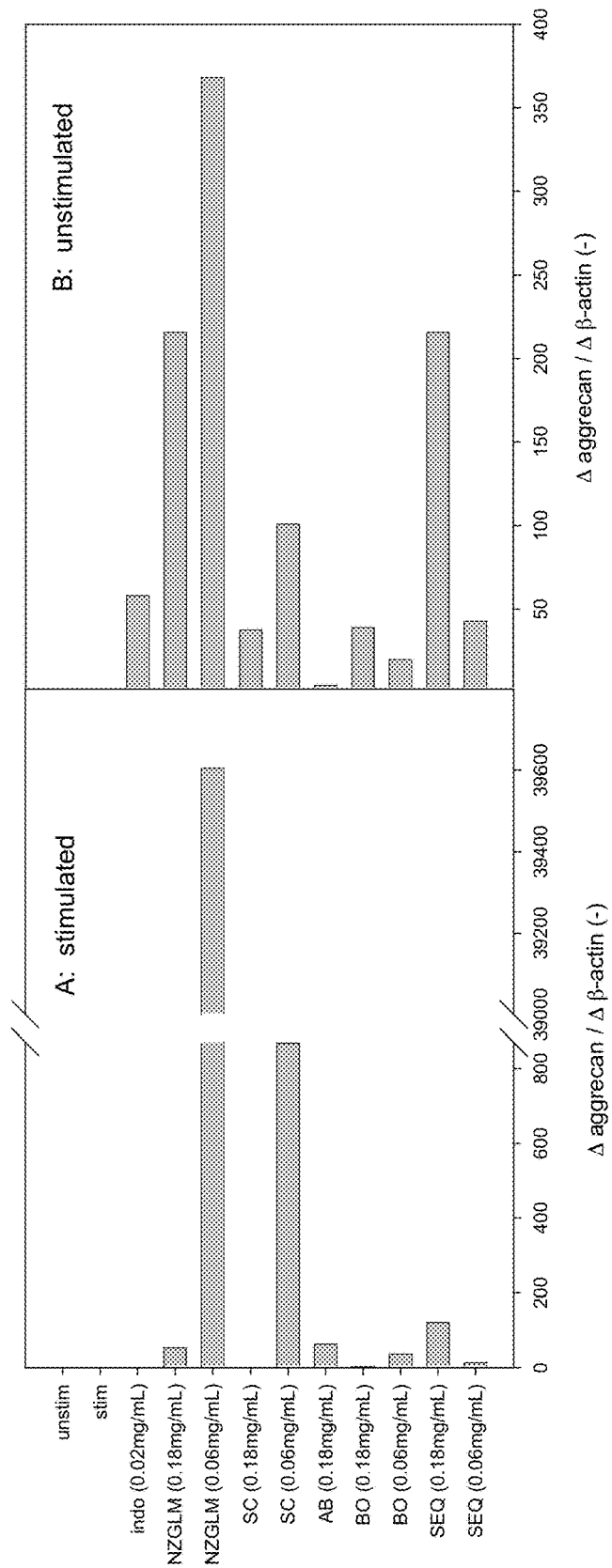
FIG. 4: Relative expression of aggrecan RNA in IL-1 stimulated (A) and unstimulated (B) cartilage explants.

Aggrecan (FIGS. 4, A and B): Stimulation of control explants with IL-1 resulted in a slight, non-significant decline in aggrecan expression. Conditioning of unstimulated explants with $indo_{sim}$ resulted in 58-fold increase in aggrecan. This increase was completely abolished by stimulation of indo$_{sim}$-conditioned explants with IL-1.

SEQ and all of its constituents significantly increase aggrecan expression in unstimulated explants. SEQ$_{sim}$ increased aggrecan expression in unstimulated explants in a dose-dependent manner (42.8 and 215.7-fold increase for 0.06 and 0.18 mg/mL, respectively).

Stimulation of conditioned explants with IL-1 resulted in significant increase in aggrecan expression in SEQ and all of its constituents, with the exception of SC$_{sim}$ (0.18 mg/mL; 1.4-fold increase).

Tissue Culture Experiments:

PGE$_2$ (FIGS. 5, A and B): Stimulation of control explants with IL-1 (10 ng/mL) resulted in a significant increase in media [PGE$_2$] over the 48 h stimulation period, resulting in a significant difference between stimulated and unstimulated controls (p=0.03). Indo$_{sim}$ (0.02 mg/mL) significantly reduced media [PGE$_2$] in IL-1 stimulated and unstimulated explants compared with stimulated and unstimulated controls, respectively. There was no IL-1-induced increase in media [PGE$_2$] in explants conditioned with indo$_{sim}$.

Figure 5:
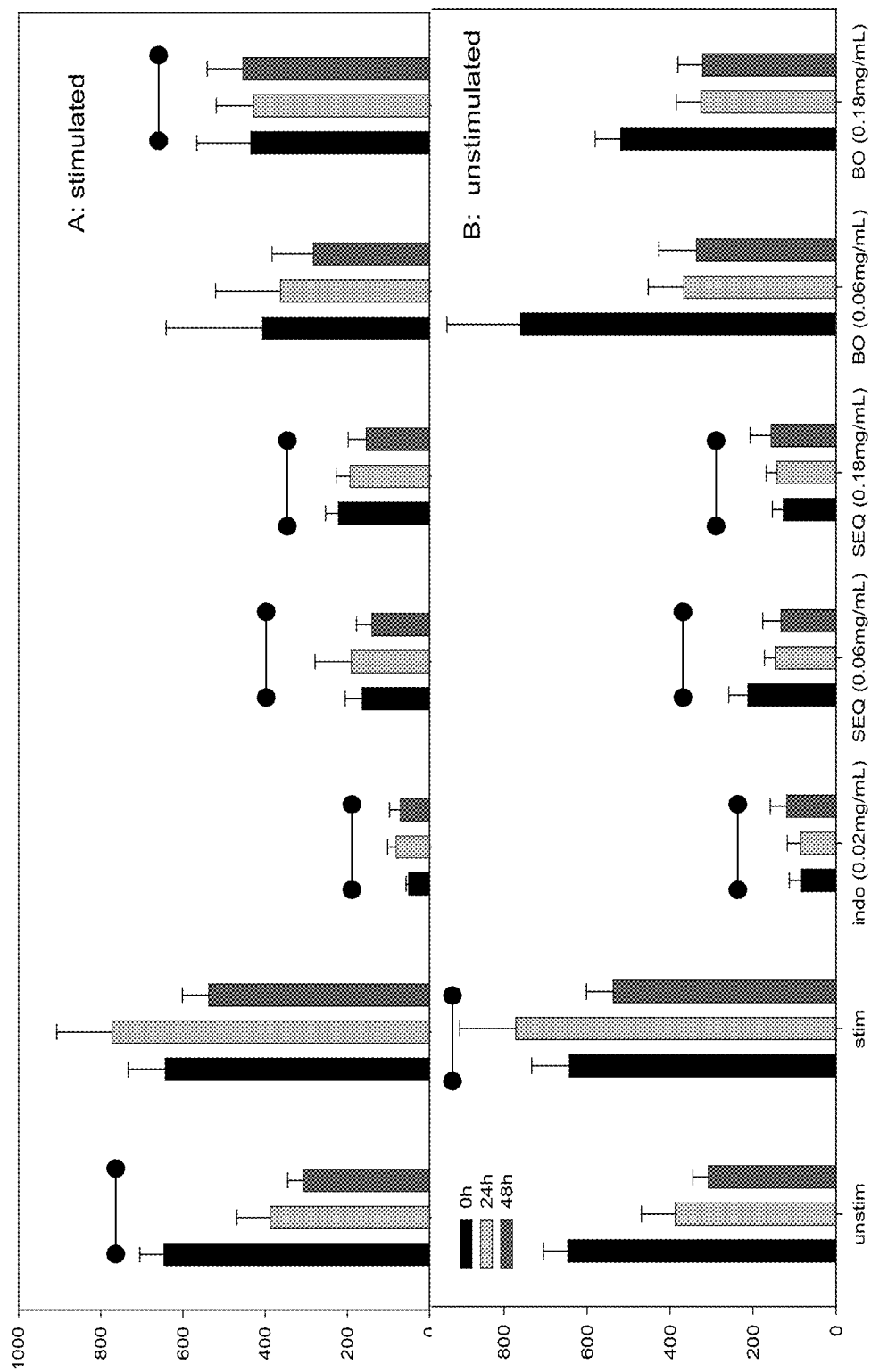
FIG. 5: Prostaglandin $E_2$ ($PGE_2$) production by IL-1 stimulated (A) and unstimulated (B) cartilage explants.

Stimulation with IL-1 of explants conditioned with SEQ$_{sim}$ (0.06 and 0.18 mg/mL) did not increase media [PGE$_2$]. Media [PGE$_2$] was significantly lower in these explants compared with stimulated and unstimulated control explants (FIG. 5, A). In unstimulated explants media [PGE$_2$] was significantly lower in explants conditioned with SEQ$_{sim}$ (0.06 and 0.18 mg/mL) than in unstimulated controls (FIG. 5, B). There was no significant difference in media [PGE$_2$] between SEQ$_{sim}$ (0.06 and 0.18 mg/mL) and indo$_{sim}$ in both IL-1-stimulated and unstimulated explants.

There was no increase in media [PGE$_2$] subsequent to IL-1 exposure in explants conditioned with BO$_{sim}$ (0.06 and 0.18 mg/mL) (FIG. 5, A). Conditioning of IL-1-stimulated explants with BO$_{sim}$ (0.18 mg/mL) resulted in a significantly lower media [PGE$_2$] than stimulated controls. There was no significant effect of BO$_{sim}$ on unstimulated explants (FIG. 5, B).

NO: There was no significant change in media [NO] in unstimulated control explants. Exposure of control explants to IL-1 (10 ng/mL) resulted in a significant elevation of media [NO] at 24 (1.21±0.1 μg/mL) and 48 h (1.06±0.1 μg/mL). There was no significant effect of indo$_{sim}$ on [NO] in stimulated or unstimulated explants (FIG. 7).

Discussion

These experiments assist in describing effects of the simulated digest of SEQ on cox 1, cox 2, iNOS, and aggrecan gene expression. The gene expression data can then be used to make predictions about the mechanism of action of SEQ.

Alterations in gene expression observed in IL-1-stimulated control explants showed a pattern consistent with an inflammatory response. IL-1 stimulation resulted in a small, non-significant increase in cox 1 expression coupled with a significant increase in cox 2 expression, as has been reported by other authors (Kydd et al., 2007).

As shown, indo$_{sim}$ showed a cox 1:cox 2 inhibition profile of about 2:1, which is consistent with its classification as a cox 1/2 inhibitor (Gerstenfeld et al., 2003). We have also shown that indo$_{sim}$ does not inhibit IL-1-induced iNOS expression, consistent with reports by other authors (Palmer et al., 1993). Nor did it influence IL-1-mediated aggrecan expression in IL-1-stimulated explants, an effect that has been reported in mechanically stressed cartilage explants (Iimoto et al., 2005).

These data characterize indomethacin as an effective anti-inflammatory predominately through cox inhibition. Its inability to reduce IL-1-mediated aggrecan expression and its augmenting effect on IL-1-mediated iNOS expression, however, suggest that cartilage exposed to indomethacin would continue to degenerate through decline in matrix formation and would suffer from increased nitric oxide-mediated cell death. Indeed these adverse effects have been reported in arthritic dogs using prophylactic indomethacin (Hungin and Kean 2001), and indomethacin is associated with worsening of some pathophysiological indicators of arthritis in humans (Rashad et al., 1989; Huakinsson et al., 1995). When indo$_{sim}$ was applied to cartilage explants in the current study, there was an increase in IL-1-mediated NO production, but this was not coupled with a decrease in cell viability.

The relative inhibitory profile of SEQ$_{sim}$ on cox 1:cox 2 expression was approximately 1:1 at both doses. In the experiments described herein, SEQ$_{sim}$ at the lower dose was comparable to indo$_{sim}$ as a cox 2 inhibitor, whereas the higher dose was a more effective inhibitor of cox 2 than indo$_{sim}$. It is therefore predicted that SEQ$_{sim}$ should effectively inhibit PGE$_2$ production by IL-1-stimulated explants.

This inhibition was observed in the tissue culture explant experiment. Inhibition of IL-1-mediated PGE$_2$ production by SEQ$_{sim}$-conditioned cartilage explants was significant at both doses, and was not statistically different from PGE$_2$ inhibition by indo$_{sim}$. This provides an explanation for the observed clinical benefit of SEQ in relieving pain in arthritic patients (Rukwied et al., 2007; Zhao et al., 2007).

Earlier publications have reported that SC$_{sim}$ and NZGLM$_{sim}$ inhibit PGE$_2$ production by IL-1-stimulated cartilage explants (Pearson et al., 2007), and the data in this application shows that BO$_{sim}$ also has this effect. However, it is of interest that, with the exception of SC$_{sim}$ (0.18 mg/mL), cox 2 inhibition by the most effective dose of SEQ$_{sim}$ is stronger than any single constituents alone. This points to a synergistic relationship between the constituents.

Given the effective PGE$_2$-inhibiting, and related cox-inhibiting properties of SEQ$_{sim}$, the effects of SEQ$_{sim}$ on iNOS were investigated. With a standard 'NSAID-like' mechanism it is predicted that SEQ would also augment iNOS expression in IL-1-stimulated explants. In fact, the opposite was true, and SEQ$_{sim}$ was found to significantly and strongly inhibit iNOS expression.

The effect of IL-1 on cellular expression of iNOS and cox 2 is differentially regulated through activation of at least 2 Mitogen Activated Protein Kinases (MAPKs) (LaPointe and Isenovi 1999). Net expression of iNOS and cox 2 are at least partially dependent on the relative amounts of pericellular NO and PGE$_2$ (Shin et al., 2007). Thus, products which increase pericellular NO can effectively downregulate expression of cox 2, and vice versa (Shin et al., 2007; Kim et al., 2005). This provides some explanation as to why SEQ$_{sim}$ showed a significant inhibitory effect on iNOS while many of the individual constituents, including shark cartilage, *Biota* and NZGLM$_{sim}$ (0.18 mg/mL), actually upregulated expression of iNOS.

Conclusions

SEQ is capable of effectively downregulating RNA for iNOS and cox 2. Its effect on iNOS and cox 2 appears to be due to synergy between its four constituents, but it may be related to post-translational inhibition of NO production (Pearson et al., 2007).

Models of cartilage inflammation in horses are widely reported, and include intra-articular challenges such as lipopolysaccharide (Jacobsen et al., 2006), Freunds Complete Adjuvant (Toutain and Cester 2004) or Na-monoiodo-acetate (Welch et al., 1991); or surgical disruptions including creation of osteochondral fragments (Frisbie et al., 2007), focal contusion impact injuries (Bolam et al., 2006) and ligamentous transsection (Simmons et al., 1999). While these models capably demonstrate maximal activation of a complexity of inflammatory mechanisms within cartilage and associated subchondral bone and soft tissues, they represent a predominately traumatic inflammatory response. They are less representative of the more subtle biochemical, functional and pathophysiological changes in incipient or sub-acute articular inflammation that characterize most cases of lameness in racing horses (Steel et al., 2006).

While non-steroidal anti-inflammatory drugs (NSAIDs) and corticosteroids remain important therapeutic resources for treatment of overt clinical lameness, nutraceuticals are becoming widespread as a therapeutic and prophylactic management strategy for horses with low-grade, sub-acute articular damage and for those at risk of developing articular problems (Trumble 2005; Neil et al., 2005). Most research reported on the efficacy and/or safety of these products in arthritis uses in vitro models (Pearson et al., 2007; Chan et al., 2006), or traumatic injury or clinical in vivo research in non-equine species (McCarthy et al., 2006; Cho et al., 2003). Though useful as screening tools, in vitro models cannot account for the systemic effects of a dietary product which may influence outcomes in the articular space.

The objectives of this section are to a) produce and characterize a reversible, sub-clinical model of IL-1-induced intra-articular inflammation in the horse with respect to $PGE_2$ and NO production, and GAG release from cartilage; and b) to apply this model to the evaluation of SEQ in mammals, particularly in horses.

Method

Diets:

SEQ powder was prepared by combining Abalone (AB), New Zealand Green Lipped Mussel (NZGLM), Shark cartilage (SC) and *Biota* oil (Interpath Pty Ltd, Australia) according to the composition provided in Table 2. SEQ mixed ration was prepared by combining SEQ powder (10 g/kg), molasses (20 g/kg) and flavoring (Essential Sweet Horse Essence D 2344. Essentials Inc. Abbotsford, BC.) (1 g/kg) to a sweet feed horse ration (Table 2), and blending in a diet mixer in 5 kg batches until fully mixed. Control ration (CON) was prepared using the same sweet feed diet blended with molasses (~20 g/kg) and flavoring (1 g/kg).

Horses:

11 healthy horses without signs of articular inflammation (3 thoroughbred, 8 standardbred; age 5-12 years; 10 geldings, 1 mare) were randomly allocated to either Group A (SEQ; 1.5 kg/day; n=6) or Group B (CON; 1.5 kg/day; n=5). The 28-day experiment consisted of two phases—Phase 1: pretreatment (14 days); Phase 2: treatment (14 days). Supplementation began on Day 0 and continued for the duration of the experiment (FIG. 6). Sample collection occurred on days 0 (pre), 14 (inj-1), 15 (2 samples: inj-2— taken immediately before injection; inj-2-2—taken 8 h post-injection), 16 (day 1), 18 (day 3), 21 (day 7) and 28 (day 14); on these days blood was collected from the jugular vein, and synovial fluid was sampled from both intercarpal joints by aseptic arthrocentesis (see below). An inflammatory challenge—recombinant interleukin-1β (IL-1)—was injected into the left or right intercarpal joint on day 14 (inj-1; 10 ng in 500 μL sterile saline) and 15 (inj-2; 100 ng in 500 μL sterile saline). An equal volume of sterile saline was injected into the contralateral intercarpal joint. Joint circumference as an indicator of joint effusion was measured with a tape measure at each sampling of joint fluid.

All horses were turned out in paddocks during the day and housed in box-stalls overnight. They were bedded on wood shavings and offered hay, water and mineral salts ad libitum. All procedures were approved by the University of Guelph Animal Care Committee in accordance with guidelines of the Canadian Council on Animal Care.

Arthrocentesis: The knees of both the left and right legs were shaved, and the area aseptically prepared using chlorhexadine (4%), and rinsed with 70% isopropyl alcohol. A sterile 22 gauge, 1.5" needle was inserted into the lateral aspect of the left intercarpal joint. A 3 cc sterile syringe was then attached, and approximately 1.5-2 mL of synovial fluid was aspired and immediately injected into a sterile $K_2$-heparin vacutainer. The procedure was then repeated for the right intercarpal joint. On days 14 (inj-1) and 15 (inj-2), IL-1 (500 μL) was injected into either the right or left intercarpal (500 μL saline injected into contralateral joint) after aspiration of synovial fluid and before removal of the needle hub. Approximately 1.5 mL of synovial fluid was removed from the vacutainer and placed into a microcentrifuge tube and spun at 11,000×g for 10 minutes to remove cellular debris. Supernatant was placed into another microcentrifuge tube containing 10 μg indomethacin, and frozen at −80° C. until analyzed for $PGE_2$, GAG and NO. Indomethacin was added to synovial fluid after it was collected in order to prevent further formation of $PGE_2$ during storage of samples. The remaining ~0.5 mL synovial fluid was sent to the Animal Health Laboratory (University of Guelph) for cytological analysis.

Synovial Fluid Cytology 1.0-1.5 mL of fluid was removed from the vacutainer for $PGE_2$, NO and GAG analysis (see below), and approximately 0.5 mL was analyzed for total nucleated cell count (Coulter Z2 counter; Beckman Coulter Canada Inc. Mississauga ON), protein (refractometer) and cell differential (on 100 nucleated cells) at the Animal Health Laboratory.

Synovial Fluid [$PGE_2$]:

Synovial fluid was thawed to room temperature then incubated with 20 μL hyaluronidase (10 mg/mL) on a tube rocker for 30 minutes at 37° C. to digest hyaluronic acid. Sample was then diluted 1:2 with formic acid (0.1%), and centrifuged 12,000×g for 10 minutes. The supernatant was decanted and analyzed for $PGE_2$ by a commercially available ELISA kit (GE Amersham, Baie D'Urfé, Québec). $PGE_2$ was extracted from the sample using provided lysis reagents to dissociate $PGE_2$ from soluble membrane receptors and binding proteins, and then quantified according to kit protocol. Plates were read using a Victor 3 microplate reader (Perkin Elmer, Woodbridge ON) with absorbance set at 450 nm. A best-fit $3^{rd}$ order polynomial standard curve was developed for each plate ($R^2 \geq 0.99$), and these equations were used to calculate $PGE_2$ concentrations for samples from each plate.

Synovial Fluid [GAG]:

Hyaluronic acid in synovial fluid samples were digested with hyaluronidase as described above. GAG concentration of synovial fluid was determined using a 1,9-DMB spectrophotometric assay as described by Chandrasekhar et al. (1987). Samples were diluted 1:3 with dilution buffer and placed into a 96-well microtitre plate. Guanidine hydrochloride (275 g/L) was added to each well followed immediately by addition of 150 μL, DMB reagent. Plates were incubated in the dark for 10 minutes, and absorbance was read on a Victor 3 microplate reader at 530 nm. Sample absorbance was compared to that of a bovine chondroitin sulfate standard (Sigma, Oakville ON). A best-fit linear standard curves was developed for each plate ($R^2 \geq 0.99$), and these equations were used to calculate GAG concentrations for samples on each plate.

Synovial Fluid [NO]:

Nitrite ($NO_{2-}$), a stable oxidation product of NO, was analyzed by the Griess reaction (Fenton et al., 2002). Undiluted TCM samples were added to 96 well plates. Sulfanilamide (0.01 g/mL) and N-(1)-Napthylethylene diamine hydrochloride (1 mg/mL) dissolved in phosphoric acid (0.085 g/L) was added to all wells, and absorbance was read within 5 minutes on a Victor 3 microplate reader at 530 nm. Sample absorbance was compared to a sodium nitrite standard.

Data Analysis and Presentation

Two-way repeated measures (RM) analysis of variance (ANOVA) was used to detect differences between treatments. When a significant F-ratio was obtained, the Holm Sidak post-hoc test was used to identify differences between treatments. One-way RM ANOVA was used to detect differences within treatments with respect to time. For blood and synovial fluid data, one-way comparisons of data were made against pre- and inj-1 data, as each represented baseline for diet and IL-1 injections, respectively. Data are presented as means±SEM. Graphs for biochemistry and hematology data are scaled to physiological reference intervals unless otherwise stated. Reference intervals are those published by the Animal Health Laboratory, University of Guelph (http://www.labservices.uoguelph.ca/units/ahl/files/AHL-userguide.pdf).

Results

Synovial Fluid $PGE_2$:

CON Horses:

There was no significant change in synovial fluid [$PGE_2$] in saline-injected joints at any time (FIG. 7, A). Relative to pre-injection concentrations, [$PGE_2$] was significantly increased at inj-2-2 (321.3±161.8 pg/mL; p=0.04) in IL-1-injected joints, at which time synovial fluid [$PGE_2$] was significantly higher in IL-1-injected joints than in saline-injected joints ($p<0.001$).

SEQ Horses:

Data represent n=5, as one outlier horse was removed from the analysis. $PGE_2$ did not change in saline-injected joints of SEQ horses. Like CON horses, there was a spike in [$PGE_2$] increased at inj-2-2 (175.4±89.2 pg/mL) in IL-1-injected joints of SEQ horses (FIG. 7, B). However, this increase was not significant when compared with pre-injection concentrations. $PGE_2$ response to saline injection was not different in SEQ horses compared with CON horses. There was no significant difference in $PGE_2$ response to IL-1 injection compared with saline in SEQ horses.

Although mean [$PGE_2$] at inj-2-2 in SEQ horses was approximately 55% that of CON horses, variability about the means resulted in no significant difference between diets.

GAG:

CON Horses:

Synovial fluid [GAG] increased in saline-injected joints between inj-1 (18.3±6.8 µg/mL) and day 1 (48.1±9.6 µg/mL) (FIG. 8, A). Injection of IL-1 (10 ng) caused a rapid and significant increase in synovial fluid [GAG] between inj-1 (24.5±7.3 µg/mL) and inj-2 (77.6±4.4 µg/mL). Synovial fluid [GAG] remained significantly elevated in IL-1-injected joints at inj-2-2 (66.0±9.6 µg/mL) and day 1 (53.3±11.4 µg/mL) compared with pre-injection concentrations. The magnitude of increase in synovial fluid [GAG] was significantly higher in IL-1-injected joints than in saline-injected joints (p=0.003).

SEQ Horses:

Synovial fluid [GAG] tended to increase (p=0.09) in both saline- and IL-1-injected joints between pre (saline: 29.3±5.9 µg/mL; IL-1: 27.0±10.8 µg/mL) and inj-1 (saline: 85.5±28.0 µg/mL; IL-1: 83.2±27.9 µg/mL), suggesting an effect of diet on synovial fluid [GAG] (FIG. 8, B). There was no change in synovial fluid [GAG] in saline- or IL-1-injected joints over the course of the experiment. There was no significant difference in synovial fluid [GAG] of IL-1-injected and saline-injected joints.

Synovial fluid [GAG] in IL-1- and saline-injected joints was significantly higher in SEQ horses than CON horses ($p<0.001$). This difference was mainly an effect of diet, and not an effect of IL-1, as evidenced by the fact that the majority of the increase occurred prior to any IL-1 injection.

NO:

CON Horses:

Synovial fluid [NO] was low and variable over the course of the experiment in both saline- and IL-1-injected joints. There was no significant effect of either saline or IL-1 injection on NO levels in CON horses over time (data not shown). The magnitude of synovial fluid [NO] was not different between IL-1- and saline-injected joints.

SEQ Horses:

There was no change in synovial fluid [NO] in IL-1- or saline-injected joints at any time over the course of the experiment. There was no significant difference between IL-1 or saline at any time.

There was no significant effect of diet on synovial fluid [NO] in IL-1- or saline-injected joints.

Synovial Fluid Cytology:

CON Horses:

Pre-injection total cell count (0.61±0.1×10$^9$/L) was significantly elevated by provision of exogenous IL-1 (10 ng) at inj-2 (40.17±16.1×10$^9$/L). Cell count was not further increased following the $2^{nd}$ IL-1 injection (100 ng), but remained slightly (but not significantly) elevated through day 1. Inj-1 cell count in saline-injected joints (0.6±0.2×10$^9$/L) increased mildly, reaching a maximum at day 1 (6.0±2.6×10$^9$/L), but this increase was not significant. Total cell counts of saline- and IL-1 injected joints were significantly different from each other at inj-2 [ie. 24 h after the $1^{st}$ IL-1 injection (10 ng)]. The increase in cell count was due mainly to an increase in the relative percentage of neutrophils. Percent neutrophils significantly increased in both IL-1- and saline-injected joints after the first injection. Neutrophil counts significantly declined in both IL-1- and saline-injected joints between day 1 and 3 without further increase for the remainder of the experiment. There was no difference in % neutrophils between IL-1- and saline-injected joints (data not shown).

SEQ Horses:

Pre-injection total cell count (0.4±0.03×10$^9$/L) was significantly elevated by provision of exogenous IL-1 (10 ng) by inj-2 (27.5±8.7×10$^9$/L). Cell count was not further increased by inj-2-2, but remained significantly elevated through day 1. Inj-1 total cell count in saline-injected joints (0.4±0.1×10$^9$/L) increased mildly, reaching a maximum at inj-2-2 (4.0±2.6×10$^9$/L), but this increase was not significant. Total cell counts of saline- and IL-1 injected joints were significantly different from each other at inj-2 (ie. 24 h after the $1^{st}$ IL-1 injection of 10 ng), inj-2-2 (ie. 8 h after the $2^{nd}$ IL-1 injection of 100 ng), and day 1 (ie. 24 h after the $2^{nd}$ IL-1 injection of 100 ng). Percent neutrophils significantly increased in both IL-1- and saline-injected joints after the first injection. Increase in neutrophil concentration of saline-injected joints may have been attributable to minor inflammation being caused by injection trauma. Neutrophil counts (%) significantly declined in both IL-1- and saline-injected joints between day 1 and 3 with a second significant spike on day 7. There was no difference in % neutrophils between IL-1- and saline-injected joints.

There was no significant difference in the effect of SEQ and CON diets on total cells counts or % neutrophils in IL-1- or saline-injected joints.

CON Horses:

Synovial fluid [protein] was significantly increased by injection of 10 ng IL-1 (20±0.0 g/L to 39.4±4.0 g/L) (FIG. 9, A). [Protein] was not further increased by injection of 100 ng IL-1, and significantly declined 24 h after the 100 ng injection. Injection of saline also resulted in a significant increase in [protein] immediately after the first injection, returning to baseline concentrations by day 1 (25.5±1.5 g/L). The magnitude of increase in [protein] over the course of the experiment was significantly higher in IL-1-injected than saline-injected joints (p=0.01).

SEQ Horses:

Injection of 10 ng IL-1 resulted in a significant increase in synovial fluid protein on inj-2 (38.7±4.9 g/L), inj-2-2 (36.2±4.4 g/L), and day 1 (27.8±3.8 g/L) compared with inj-1 (20±0 g/L) (FIG. 9, B). There was no further effect of the $2^{nd}$ IL-1 injection of 100 ng on [protein]. Saline injection also resulted in a significant increase in [protein] on inj-2-am (27.5±3.0 g/L) and inj-2-pm (25.8±2.5 g/L) compared with inj-1 (20.6±0.6 g/L). The magnitude of increase in synovial fluid [protein] was significantly higher in IL-1-injected joints than in saline-injected joints (p=0.003).

There was no significant difference in the effect of SEQ and CON diets on synovial fluid [protein] in IL-1- or saline injected joints.

Joint Circumference:

CON Horses:

There was no significant change in circumference over time in IL-1- or saline-injected joints, and there was no significant difference in joint circumference between IL-1- and saline-injected joints (FIG. 10, A).

SEQ Horses:

There was a significant increase in joint circumference in IL-1-injected joints between inj-1 (31.1±0.2 cm) and inj-2 (31.9±0.5 cm) in SEQ horses (FIG. 10, B). Joint circumference remained significantly elevated at inj-2-2 (31.7±0.4 cm) before declining to pre-injection levels. Exactly the same pattern was shown in the saline-injected joints of SEQ horses.

Joint circumference of IL-1-injected joints was significantly lower in SEQ horses than CON horses (p<0.001).

Discussion

This data shows a minimally invasive, reversible model of early stage articular inflammation that can be used to evaluate putative anti-inflammatory nutraceuticals.

The double IL-1 injection protocol resulted in a statistically significant increase in PGE$_2$ at 8 h after the $2^{nd}$ injection. None of the CON horses were overtly lame at the walk or brief trot at any time during the experiment, despite mean peak synovial fluid [PGE$_2$] (498 pg/mL) being commensurate with that associated with lameness in horses (488 pg/mL; de Grauw et al., 2006). The increase in PGE$_2$ was not accompanied by a concomitant increase in NO. This provides a possible explanation as to why these horses were not lame, as transmission and perception of nociceptive pain occurs predominately as a result of combined effect of elevated PGE$_2$ and NO. CON horses may have demonstrated a low-grade lameness had they been subjected to moderate exercise, but this was not undertaken due to the confounding effect of exercise on synovial fluid [PGE$_2$] (van den Boom et al., 2005). The observed increase in synovial fluid [PGE$_2$] in CON horses provides good evidence for a low-grade IL-1-induced inflammation within the joint. We hypothesized that this increase would be blunted by dietary provision of an efficacious anti-inflammatory nutraceutical.

Trafficking of inflammatory cells and release of glycosaminoglycan into the synovial fluid were more sensitive to stimulation with IL-1 than production of PGE$_2$, as an increase in synovial fluid [GAG] and [neutrophils] was observed 24 h after the initial 10 ng IL-1 injection. Synovial fluid [protein] was also elevated immediately after the $1^{st}$ IL-1 injection. These parameters were not further increased by provision of a higher IL-1 challenge. These responses are consistent with a 'pre-arthritic' inflammatory state (Adarichev et al., 2006). Genes turned on in the early stage of arthritis are predominately those associated with transcription of chemokines, cytokines (notably, IL-1), and metalloproteinases, notably, MMP-13 and MMP-9. Chemokines are potent signals for inflammatory cell migration into the synovial space. As synoviocytes and endothelial cells of the synovial membrane become activated to express cell adhesion molecules and produce chemokines, neutrophil extravasation into the joint space greatly increases, as was observed in the studies described herein as a steep increase in synovial fluid [neutrophils]. Cells of the synovial membrane also become more permeable to serum proteins (Middleton et al., 2004) resulting in the observed rapid increase in synovial fluid [protein]. MMP-13 (Yammani et al., 2006) and MMP-9 (Soder et al., 2006) are key degradative enzymes in articular cartilage, and the increase in IL-1-induced synovial fluid [GAG] observed in the current study support studies demonstrating substantial upregulation of genes encoding these enzymes in early arthritis (Adarichev et al., 2006; Kydd et al., 2007). Micro-array analysis of pre-arthritic cartilage in PG-stimulated mice revealed that genes encoding for phospholipase C$_2$, the enzyme catalyzing release of arachidonic acid from nuclear membranes, was not elevated (Adarichev et al., 2006). This may explain, at least in part, why PGE$_2$ required a longer time course for elevation subsequent to IL-1 stimulation than cell migration and release of GAGs.

Intra-articular challenge with IL-1 did not result in a consistent increase in synovial fluid nitric oxide. IL-1-induced nitric oxide has been frequently reported in cartilage explant models (Pearson et al., 2007; Petrov et al. 2005), cells taken from animal models of acute articular inflammation (Kumar et al., 2006) and clinical cases of articular inflammation (Karatay et al., 2005). This data provides support for evidence that genes encoding inducible nitric oxide synthase are not upregulated in early stage arthritis (Kydd et al., 2007), which delays IL-1-induced formation of nitric oxide.

SEQ provided protection to IL-1-stimulated joints as evidenced by: 1) no significant increase in synovial fluid [PGE$_2$]; 2) increased [GAG] in the synovial fluid prior to IL-1 challenge, then preventing IL-1-induced increase in GAG; and 3) limited effusion into the joint space subsequent to IL-1 challenge.

As part of the diet for 2 weeks prior to an intra-articular IL-1 challenge, SEQ prevented significant elevation in IL-1-induced PGE$_2$. Similar to CON horses, PGE$_2$ response to IL-1 in SEQ horses peaked at 8 h after the second IL-1 injection, but the peak was lower, and did not result in statistically significant changes over time or significant differences between IL-1 and saline injection. This shows that SEQ reduces inflammation and pain associated with elevated PGE$_2$ in horses with early stage arthritis, and implies that feeding SEQ to horses prior to articular damage may impede progression of the disease to a more advanced stage.

The observed increase in synovial fluid [GAG] of SEQ horses in both saline- and IL-1-injected joints between pre and inj-1—ie. before inflammatory challenge—provides evidence for the post-absorptive accumulation of dietary GAGs within the synovial space.

The effectiveness of SEQ in preventing biochemical indicators of early-stage arthritis results from a synergistic effect of its four ingredients.

Published reports have reported significant improvement in arthritic signs in dogs provided with dietary NZGLM (Pollard et al., 2006), and significant protection by glucosamine and chondroitin—the major bioactive constituents of SC—of cartilage explants against degradation by IL-1 (Dechant et al., 2005). However, the in vitro PGE$_2$-inhibitory effect of SEQ is greater than that of any of its four constituents alone, per gram of product (Pearson et al. unpublished), suggesting a level of synergism between the ingredients.

Fractionation of *Biota* Oil

Chromatography

Oil from the seeds of *Biota Orientalis* was fractionated using an Agilent 1200 Preparative HPLC equipped with a diode array detector and an automated fraction collector. The column used was an Agilent Prep C18, 10 μm (30×250 mm) with the following gradient at a flow rate of 20 ml/minute with a 900 μL injection of Constituent 4. 0-5 minutes 80% water 20% Acetonitrile. 5-7 minutes Gradient change to 10% water 90% Acetonitrile, 7-25 minutes isocratic 10% water 90% Acetonitrile. Fraction detection was achieved at 254 nm.

Mass Spectrometry:

The mass spectrometry detection was performed on an Agilent 6210 MSD Time of Flight mass spectrometry in both positive and negative ion mode. The following electrospray ionization conditions were used, drying gas: nitrogen (7 mL min-1, 350° C.); nebuliser gas: nitrogen (15 psi); capillary voltage: 4.0 kV; vaporization temperature: 350° C. and cone voltage: 60V.

FIG. 14 shows the chromatographic spectrum of the oil, and various fractions were collected and numbered as shown.

(B) Anti-Inflammatory Potential of Fractions from *Biota* Oil

To study the anti-inflammatory activities, assays Fr 1, Fr i, Fr V and Fr Vi were selected and tested at a concentration of ≤64 μg/ml. The assays carried out to measure the 1) Nitric Oxide (NO) levels, 2) prostaglandin PGE2 levels, 3) prostaglandin PGF2α levels. NHAC cells at passage 3, were stimulated first with proinflammatory cytokine IL-1β at a predetermined concentration 10 ng/ml overnight, NHAC Cells were then treated with fractions in the presence of IL-1β 10 ng/ml for 24 hours and cell culture supernatant was collected to measure NO, PGE2 and PGF2α levels. Griess Reagent Kit for Nitrite Determination (Molecular Probes, Invitrogen) was used as per kit instructions. For estimation of PGs, High Sensitivity PGE2 & PGF2α EIA kits (Assay Designs Inc.) were used.

As shown in FIG. 15, fractions 1 (Fr 1), Fr I, and Fr V reduced the NO levels (highly significant) in a dose dependent manner. Fr1 was found to be the most effective among all the four fractions with Fr Vi the least effective, although still showing some effect.

The non steroidal anti inflammatory drug Indomethacin used as a positive control significantly reduced the IL-1β induced PGE2 levels. All the four fractions had no effect on these levels at any of the concentrations tested (FIGS. 16 & 17).

Indomethacin significantly reduced the IL-1β induced PGF2α levels. Fr 1 showed no effect at all on the PGF2α levels, while Fr i, Fr V and Fr Vi reduced these levels, in a dose dependent manner (64-32 μg/ml) (FIGS. 18 & 19).

The effectiveness of the *biota* oil extract fractions has until now not been known. The use of the compounds of F1.1-1.4 either separately or as a mixture with one or more of the other fractions provides for a remarkable improvement in the treatment of conditions, such as osteoarthritis.

Any improvement may be made in part or all of the method steps and systems components. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited as permitted by applicable law. Moreover, any combination of the above-described elements in all possible variations thereof is encompassed by the invention unless otherwise indicated herein or otherwise clearly contraindicated by context.

While the invention herein disclosed has been described by means of specific embodiments and applications thereof, numerous modifications and variations could be made thereto by those skilled in the art without departing from the scope of the invention set forth in the claims.

REFERENCES

Adarichev V A, Vermes C, Hanyecz A, Ludanyi K, Tunyogi-Csapo M, Finnegan A, Mikecz K, Glant T T. (2006) Antigen-induced differential gene expression in lymphocytes and gene expression profile in synovium prior to the onset of arthritis. Autoimmunity; 39(8):663-73.

Aoyama T, Liang B, Okamoto T, Matsusaki T, Nishijo K, Ishibe T, Yasura K, Nagayama S, Nakayama T, Nakamura T, Toguchida J. (2005) PGE2 signal through EP2 promotes the growth of articular chondrocytes. J Bone Miner Res; 20(3):377-89.

Blitek A, Ziecik A J. (2006) Role of tumour necrosis factor alpha in stimulation of prostaglandins F(2alpha) and E(2) release by cultured porcine endometrial cells. Reprod Domest Anim; 41(6):562-7.

Bolam C J, Hurtig M B, Cruz A, McEwen B J. (2006) Characterization of experimentally induced post-traumatic osteoarthritis in the medial femorotibial joint of horses. Am J Vet Res; 67(3):433-47.

Bui L M, Bierer T L. (2003) Influence of green lipped mussels (*Perna canaliculus*) in alleviating signs of arthritis in dogs. Vet Ther; 4(4):397-407.

Chan P S, Caron J P, Rosa G J, Orth M W. (2006) Glucosamine and chondroitin sulfate regulate gene expression and synthesis of nitric oxide and prostaglandin E(2) in articular cartilage explants. Osteoarthritis Cartilage; 13(5):387-94.

Chandrasekhar S, Esterman M A, Hoffman H A. (1987) Microdetermination of proteoglycans and glycosaminoglycans in the presence of guanidine hydrochloride. Anal Biochem; 161(1):103-108.

Cho S H, Jung Y B, Seong S C, Park H B, Byun K Y, Lee D C, Song E K, Son J H. (2003) Clinical efficacy and safety of Lyprinol, a patented extract from New Zealand green-lipped mussel (Perna Canaliculus) in patients with osteoarthritis of the hip and knee: a multicenter 2-month clinical trial. Allerg Immunol (Paris); 35(6):212-6.

Dechant J E, Baxter G M, Frisbie D D, Trotter G W, McIlwraith C W. (2005) Effects of glucosamine hydrochloride and chondroitin sulphate, alone and in combination, on normal and interleukin-1 conditioned equine articular cartilage explant metabolism, Equine Vet J, 37, 227-31.

Fehrenbacher A, Steck E, Rickert M, Roth W, Richter W. (2003) Rapid regulation of collagen but not metalloproteinase 1, 3, 13, 14 and tissue inhibitor of metalloproteinase 1, 2, 3 expression in response to mechanical loading of cartilage explants in vitro. Arch Biochem Biophys; 410(1):39-47

Fenton J I, Chlebek-Brown K A, Caron J P, Orth M W. (2002) Effect of glucosamine on interleukin-1-conditioned articular cartilage. Equine Vet J Suppl; (34):219-23.

Frisbie D D, Kawcak C E, Werpy N M, Park R D, McIlwraith C W. (2007) Clinical, biochemical, and histologic effects of intra-articular administration of autologous conditioned serum in horses with experimentally induced osteoarthritis. Am J Vet Res; 68(3):290-6.

Gerstenfeld L C, Thiede M, Seibert K, Mielke C, Phippard D, Svagr B, Cullinane D, Einhorn T A. (2003) Differential inhibition of fracture healing by non-selective and cyclooxygenase-2 selective non-steroidal anti-inflammatory drugs. J Orthop Res; 21(4):670-5.

Granja A G, Sabina P, Salas M L, Fresno M, Revilla Y. (2006) Regulation of inducible nitric oxide synthase expression by viral A238L-mediated inhibition of p65/RelA acetylation and p300 transactivation. J Virol; 80(21):10487-96.

Huakinsson E C, Berry H, Gishen P. (1995) Effects of anti-inflammatory drugs on the progression of osteoarthritis of the knee. J Rheumatol, 22:1941-1946.

Hungin A P, Kean W F. (2001) Nonsteroidal anti-inflammatory drugs: overused or underused in osteoarthritis? Am J Med; 110(1A):8S-11S.

Iimoto S, Watanabe S, Takahashi T, Shimizu A, Yamamoto H. (2005) The influence of Celecoxib on matrix synthesis by chondrocytes under mechanical stress in vitro. Int J Mol Med; 16(6): 1083-8.

Jacobsen S, Niewold T A, Halling-Thomsen M, Nanni S, Olsen E, Lindegaard C, Andersen P H. (2006) Serum amyloid A isoforms in serum and synovial fluid in horses with lipopolysaccharide-induced arthritis. Vet Immunol Immunopathol; 110(3-4):325-30

Karatay S, Kiziltunc A, Yildirim K, Karanfil R C, Senel K. (2005) Effects of different hyaluronic acid products on synovial fluid NO levels in knee osteoarthritis. Clin Rheumatol; 24(5):497-501.

Kida Y, Kobayashi M, Suzuki T, Takeshita A, Okamatsu Y, Hanazawa S, Yasui T, Hasegawa K. (2005) Interleukin-1 stimulates cytokines, prostaglandin E2 and matrix metalloproteinase-1 production via activation of MAPK/AP-1 and NF-kappaB in human gingival fibroblasts. Cytokine; 29(4): 159-68.

Kim S F, Huri D A, Snyder S H. (2005) Inducible nitric oxide synthase binds, S-nitrosylates, and activates cyclooxygenase-2. Science; 310(5756):1966-70.

Kumar D A, Raju K V, Settu K, Kumanan K, Puvanakrishnan R. (2005) Effect of a derivatized tetrapeptide from lactoferrin on nitric oxide mediated matrix metalloproteinase-2 production by synovial fibroblasts in collagen-induced arthritis in rats. Peptides; 27(6):1434-42.

Kusano S, Igarashi N, Sakai S, Toida T. [Effect of orally administered chondrosine on uptake of 35S sulfate into rat cartilage] Yakugaku Zasshi; 126(4):297-300.

Kydd A S, Reno C R, Tsao H W, Hart D A. (2007) Early inflammatory arthritis in the rabbit: the influence of intraarticular and systemic corticosteroids on mRNA levels in connective tissues of the knee. J Rheumatol; 34(1): 130-9.

LaPointe M C, Isenovic E. (1999) Interleukin-1beta regulation of inducible nitric oxide synthase and cyclooxygenase-2 involves the p42/44 and p38 MAPK signaling pathways in cardiac myocytes. Hypertension; 33(1 Pt 2):276-82.

Marciani L, Bush D, Wright P, Wickham M, Pick B, Wright J, Faulks R, Fillery-Travis A, Spiller R C, Gowland P A. (2005) Monitoring of gallbladder and gastric coordination by EPI. J Magn Reson Imaging; 21(1):82-85.

McCarthy G, O'donovan J, Jones B, McAllister H, Seed M, Mooney C. (2006) Randomised double-blind, positive-controlled trial to assess the efficacy of glucosamine/chondroitin sulfate for the treatment of dogs with osteoarthritis. Vet J. 2006 Apr. 27;

Mesa Garcia M D, Aguilera Garcia C M, Gil Hernandez A. (2006) Importance of lipids in the nutritional treatment of inflammatory diseases. Nutr Hosp; 21 Suppl 2:28-41, 30-43.

Middleton J, Americh L, Gayon R, Julien D, Aguilar L, Amalric F, Girard J P. (2004) Endothelial cell phenotypes in the rheumatoid synovium: activated, angiogenic, apoptotic and leaky. Arthritis Res Ther; 6(2):60-72.

Neil K M, Caron J P, Orth M W. (2005) The role of glucosamine and chondroitin sulfate in treatment for and prevention of osteoarthritis in animals. J Am Vet Med Assoc; 226(7):1079-88.

Nishimoto S, Takagi M, Wakitani S, Nihira T, Yoshida T. (2005) Effect of chondroitin sulfate and hyaluronic acid on gene expression in a three-dimensional culture of chondrocytes. J Biosci Bioeng; 100(1):123-6.

Palmer R M, Hickery M S, Charles I G, Moncada S, Bayliss M T. (1993) Induction of nitric oxide synthase in human chondrocytes. Biochem Biophys Res Commun; 193(1): 398-405.

Pearson W, Orth M W, Karrow N A, MacLusky N, Lindinger M I (2007) Anti-inflammatory and chondroprotective effects of nutraceuticals in a cartilage explant model of inflammation. Mol Nutr Food Res: 2007, 51, 1020-1030.

Petrov R, MacDonald M H, Tesch A M, Benton H P. (2005) Inhibition of adenosine kinase attenuates interleukin-1- and lipopolysaccharide-induced alterations in articular cartilage metabolism. Osteoarthritis Cartilage; 13(3):250-7.

Pivnenko T N, Sukhoverkhova GIu, Epshtein L M, Somova-Isachkova L M, Timchenko N F, Besednova N N. (2005) [Experimental morphological study of the therapeutic effect of shark cartilage preparation in a model of infective allergic arthritis] Antibiot Khimioter; 50(5-6):20-3.

Pollard B, Guilford W G, Ankenbauer-Perkins K L, Hedderley D. (2006) Clinical efficacy and tolerance of an extract of green-lipped mussel (*Perna canaliculus*) in dogs presumptively diagnosed with degenerative joint disease. N Z Vet J; 54(3):114-8.

Rashad S, Revell P, Hemingway A, Low F, Rainsford K, Walker F. (1989) Effect of non-steroidal anti-inflammatory drugs on the course of osteoarthritis. Lancet; 2(8662):519-22.

Rininger J A, Kickner S, Chigurupati P, McLean A, Franck Z. (2000) Immunopharmacological activity of *Echinacea* preparations following simulated digestion on murine macrophages and human peripheral blood mononuclear cells. J Leukoc Biol; 68(4):503-10.

Rukwied R, Chizh B A, Lorenz U, Obreja O, Margarit S, Schley M, Schmelz M. (2007) Potentiation of Nociceptive Responses to Low pH Injections in Humans by Prostaglandin E2. J Pain. 2007 May; 8(5):443-51.

Schena M, Shalon D, Davis R W, Brown P O. (1995) Quantitative monitoring of gene expression patterns with a complementary DNA microarray. *Science;* 270:467-470.

Shen C L, Hong K J, Kim S W. (2005) Comparative effects of ginger root (*Zingiber officinale* Rosc.) on the production of inflammatory mediators in normal and osteoarthrotic sow chondrocytes. J Med Food; 8(2):149-53.

Shin J I, Lee Y K, Kim Y M, Hwang J T, Park O J. (2007) Possible link between NO concentrations and COX-2 expression in systems treated with soy-isoflavones. Ann N Y Acad Sci; 1095:564-73.

Simmons E J, Bertone A L, Weisbrode S E. (1999) Instability-induced osteoarthritis in the metacarpophalangeal joint of horses. Am J Vet Res; 60(1):7-13.

Soder S, Roach H I, Oehler S, Bau B, Haag J, Aigner T. (2006) MMP-9/gelatinase B is a gene product of human adult articular chondrocytes and increased in osteoarthritic cartilage. Clin Exp Rheumatol; 24(3):302-4.

Steel C M, Hopper B J, Richardson J L, Alexander G R, Robertson I D. (2006) Clinical findings, diagnosis, prevalence and predisposing factors for lameness localised to the middle carpal joint in young Standardbred racehorses. Equine Vet J; 38(2):152-7.

Su X Q, Antonas K N, Li D. (2004) Comparison of n-3 polyunsaturated fatty acid contents of wild and cultured Australian abalone. Int J Food Sci Nutr; 55(2):149-54.

Toutain P L, Cester C C. (2004) Pharmacokinetic-pharmacodynamic relationships and dose response to meloxicam in horses with induced arthritis in the right carpal joint. Am J Vet Res; 65(11):1533-41.

Trumble T N. (2005) The use of nutraceuticals for osteoarthritis in horses. Vet Clin North Am Equine Pract; 21(3): 575-97, v-vi.

van den Boom R, van de Lest C H, Bull S, Brama R A, van Weeren P R, Barneveld A. (2005) Influence of repeated arthrocentesis and exercise on synovial fluid concentrations of nitric oxide, prostaglandin E2 and glycosaminoglycans in healthy equine joints. Equine Vet J; 37(3):250-6.

Welch R D, Watkins J P, DeBowes R M, Leipold H W. (1991) Effects of intra-articular administration of dimethylsulfoxide on chemically induced synovitis in immature horses. Am J Vet Res; 52(6):934-9.

Yammani R R, Carlson C S, Bresnick A R, Loeser R F. (2006) Increase in production of matrix metalloproteinase 13 by human articular chondrocytes due to stimulation with S100A4: Role of the receptor for advanced glycation end products. Arthritis Rheum; 54(9):2901-11.

Yang I V, Chen E, Hasseman J P, Liang W, Frank B C, Wang S, Sharov V, Saeed A I, White J, Li J, Lee N H, Yeatman T J, Quackenbush J. (2002) Within the fold: assessing differential expression measures and reproducibility in microarray assays. Genome Biol; 3(11):0062.

Zhao P, Waxman S G, Hains B C. (2007) Extracellular signal-regulated kinase-regulated microglia-neuron signaling by prostaglandin $E_2$ contributes to pain after spinal cord injury. J Neurosci; 27(9):2357-68.

What is claimed is:

1. A method of treating joint inflammation in a mammal in need thereof, the method comprising:
   obtaining hydrolyzed *Biota orientalis* seed oil; and
   administering a nutraceutical composition including an effective amount of the hydrolyzed *Biota orientalis* seed oil to said mammal.

2. The method of claim 1, wherein the composition inhibits COX expression.

3. The method of claim 1, wherein the nutraceutical composition further comprises mussel extract.

4. The method of claim 2, wherein the COX is COX-2.

5. The method of claim 1, wherein the hydrolyzed *Biota orientalis* seed oil is obtained by:
   adding *Biota orientalis* seed oil to an alkaline solution;
   neutralizing said alkaline solution to a pH of about 4.5; and
   separating a non-aqueous phase from the alkaline solution to provide the hydrolyzed *Biota orientalis* seed oil.

6. The method of claim 5, wherein said alkaline solution is neutralized to a pH of about 4.5 by the addition of 36% sulfuric acid.

7. The method of claim 5, wherein said alkaline solution is a solution of about 1:2.9:1.4 (w/w) KOH:EtOH:cold water.

8. A method for treating joint inflammation in a mammal in need thereof, the method comprising:
   obtaining hydrolyzed *Biota orientalis* seed oil; and
   administering a nutraceutical composition including an effective amount of the hydrolyzed *Biota orientalis* seed oil to said mammal, wherein said hydrolyzed *Biota orientalis* seed oil is obtained by:
   adding *Biota orientalis* seed oil to an alkaline solution of about 1:2.9:1.4 (w/w) KOH:EtOH:cold water;
   neutralizing said alkaline solution to a pH of about 4.5; and
   separating a non-aqueous phase from said alkaline solution to yield the hydrolyzed *Biota orientalis* seed oil.

9. The method of claim 8, wherein the adding of said *Biota orientalis* seed oil to said alkaline solution provides in a mixture, and wherein said mixture is kept at about 40° C. for about 1.5 hours under an inert atmosphere.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: Forward primer for porcine Cox1 gene (AF207823)

<400> SEQUENCE: 1
gggagtcctt ctccaatgtg                                             20

<210> SEQ ID NO 2
<211> LENGTH: 20
<212> TYPE: DNA
<213> ORGANISM: Artificial
<220> FEATURE:
<223> OTHER INFORMATION: Reverse primer for porcine Cox1 gene (AF207823)

<400> SEQUENCE: 2
cataaatgtg gccgaggtct                                             20

<210> SEQ ID NO 3
<211> LENGTH: 20
<212> TYPE: DNA
<213> ORGANISM: Artificial
```

```
<220> FEATURE:
<223> OTHER INFORMATION: Forward primer for porcine Cox2 gene (AF207824)

<400> SEQUENCE: 3
atgatctacc cgcctcacac                                                   20

<210> SEQ ID NO 4
<211> LENGTH: 20
<212> TYPE: DNA
<213> ORGANISM: Artificial
<220> FEATURE:
<223> OTHER INFORMATION: Reverse primer for porcine Cox2 gene (AF207824)

<400> SEQUENCE: 4
aaaagcagct ctgggtcaaa                                                   20

<210> SEQ ID NO 5
<211> LENGTH: 21
<212> TYPE: DNA
<213> ORGANISM: Artificial
<220> FEATURE:
<223> OTHER INFORMATION: Forward primer for porcine iNOS gene (X98196)

<400> SEQUENCE: 5
tgcgttatgc caccaacaat g                                                 21

<210> SEQ ID NO 6
<211> LENGTH: 19
<212> TYPE: DNA
<213> ORGANISM: Artificial
<220> FEATURE:
<223> OTHER INFORMATION: Reverse primer for porcine iNOS gene (X98196)

<400> SEQUENCE: 6
actctccagg atgttgtag                                                    19

<210> SEQ ID NO 7
<211> LENGTH: 19
<212> TYPE: DNA
<213> ORGANISM: Artificial
<220> FEATURE:
<223> OTHER INFORMATION: Forward primer for porcine Aggrecan gene
      (AF201722)

<400> SEQUENCE: 7
caggagaaga gatgccaac                                                    19

<210> SEQ ID NO 8
<211> LENGTH: 18
<212> TYPE: DNA
<213> ORGANISM: Artificial
<220> FEATURE:
<223> OTHER INFORMATION: Reverse primer for porcine Aggrecan gene
      (AF201722)

<400> SEQUENCE: 8
caggtgatcc gaggctcc                                                     18

<210> SEQ ID NO 9
<211> LENGTH: 17
<212> TYPE: DNA
<213> ORGANISM: Artificial
<220> FEATURE:
<223> OTHER INFORMATION: Forward primer for porcine beta-actin gene
      (SSU07786)

<400> SEQUENCE: 9
```

```
tgcaggtgac catggcc                                                      17

<210> SEQ ID NO 10
<211> LENGTH: 21
<212> TYPE: DNA
<213> ORGANISM: Artificial
<220> FEATURE:
<223> OTHER INFORMATION: Reverse primer for porcine beta-actin gene
      (SSU07786)

<400> SEQUENCE: 10
cggtaatgga acacaacccc t                                                 21
```